United States Patent [19]

Shepherd et al.

[11] Patent Number: 5,061,632

[45] Date of Patent: Oct. 29, 1991

[54] CAPILLARY TUBE HEMOGLOBINOMETER AND OXIMETER

[75] Inventors: A. P. Shepherd; John M. Steinke, both of San Antonio, Tex.

[73] Assignee: Board of Regents, The University of Texas System, Austin, Tex.

[21] Appl. No.: 304,744

[22] Filed: Jan. 31, 1989

[51] Int. Cl.$^5$ .......... G01N 21/51

[52] U.S. Cl. .......... 436/66; 356/41; 356/339; 356/341; 422/73; 422/82.05; 436/68; 436/67

[58] Field of Search .......... 422/73, 82.05; 436/66, 436/68, 69; 356/41, 339, 341

[56] References Cited

U.S. PATENT DOCUMENTS

| | | |
|---|---|---|
| 30,007 | 5/1879 | Steuer et al. . |
| 2,878,715 | 3/1959 | Rhees . |
| 3,296,922 | 1/1967 | Goldberg . |
| 3,527,542 | 6/1966 | Penhasi et al. . |
| 3,638,640 | 2/1972 | Shaw . |
| 3,692,410 | 9/1972 | Jurany et al. . |
| 3,764,267 | 10/1973 | Farr . |
| 3,799,672 | 3/1974 | Vurek . |
| 3,972,614 | 8/1976 | Johansen et al. . |
| 3,994,585 | 11/1976 | Frey . |
| 4,003,662 | 1/1977 | Retzer et al. . |
| 4,013,417 | 3/1977 | Raffaele . |
| 4,057,394 | 11/1977 | Genshaw . |
| 4,134,678 | 1/1979 | Brown et al. . |
| 4,240,749 | 12/1980 | Retzer . |
| 4,243,883 | 1/1981 | Schwarzmann . |
| 4,301,412 | 11/1981 | Hill et al. . |
| 4,303,887 | 12/1981 | Hill et al. . |
| 4,308,029 | 12/1981 | Siggaard-Andersen . |
| 4,324,556 | 4/1982 | Robertson et al. . |
| 4,357,105 | 11/1982 | Loretz . |
| 4,444,498 | 4/1984 | Heinemann . |
| 4,453,266 | 6/1984 | Bacus . |
| 4,502,786 | 3/1985 | Golias et al. . |
| 4,565,448 | 1/1986 | Abbott et al. . |
| 4,605,305 | 8/1986 | Lenoir et al. . |
| 4,651,741 | 5/1987 | Passafaro . |
| 4,700,708 | 10/1987 | New, Jr. et al. . |

OTHER PUBLICATIONS

J. W. Kiel and A. P. Shepherd, "A Microcomputer Oximeter for Whole Blood", *Amer. J. Physiol.*, vol. 244, pp. H722–H725, 1983.

J. M. Steinke and A. P. Shepherd, "Role of Light Scattering in Whole Blood Oximetry", *IEEE Transactions on Biomedical Engineering*, vol. BME-33, No. 3, Mar. 1986.

N. M. Anderson and P. Sekelj, "Light-Absorbing and Scattering Properties of Non-Haemolysed Blood", *Phys. Med. Biol.*, vol. 12, pp. 173–184, 1967.

K. Kramer, J. O. Elam, G. A. Saxton and W. N. Elam, Jr., "Influence of Oxygen Saturation, Erythrocyte Concentration and Optical Depth Upon the Red and Near-Infrared Light Transmittance of Whole Blood", *Amer. J. Physiol.*, vol. 165, pp. 229–246, Apr. 1951.

(List continued on next page.)

*Primary Examiner*—Jill Johnston

*Attorney, Agent, or Firm*—Arnold, White & Durkee

[57] ABSTRACT

An oximeter that measures both the total hemoglobin concentration in whole, undiluted blood and the percentage of the hemoglobin saturated with oxygen. The oximeter uses red and infrared light-emitting diodes to illuminate a capillary tube filled with a sample of whole, undiluted blood. Light scattered by the blood travels a short distance down the length of the capillary tube and reaches a photodetector, the output of which is amplified, digitized, and fed to a microprocessor. The microprocessor computes the total hemoglobin concentration as a nonlinear monotonic function of the infrared light intensity. Oxyhemoglobin saturation is computed from the ratio of the logarithms of the intensities of red and infrared light. The invention provides a measurement of oxygen saturation without calibration shifts present in other oximeters due to fluctuations in total hemoglobin concentration. In addition, the present invention is accurate over a wide range of oxygen saturation, and the blood samples are not diluted or hemolyzed and can thus be preserved for further analysis.

18 Claims, 7 Drawing Sheets

OTHER PUBLICATIONS

F. J. Janssen, "A Study of the Absorption and Scattering Factors of Light in Whole Blood", Med. Biol. Eng., vol. 10, pp. 231-240, 1972.

D. L. Drabkin, "The Crystallographic and Optical Properties of the Hemoglobin of Man in Comparison with Those of Other Species", *J. Biol. Chem.*, vol. 164, pp. 703-723, 1946.

Setsuo Takatani, Hiroyuki Noda, Hisateru Takano and Tetsuzo Akutsu, "A Miniature Hybrid Reflection Type Optical Sensor for Measurement of Hemoglobin Content and Oxygen Saturation of Whole Blood", *IEEE Transactions on Biomedical Engineering,* vol. 34, No. 3, Mar. 1988.

M. Singh and K. P. Joseph, "Optical Method for Haematocrit determination", Med. & Biol. Eng. & Comput., vol. 20, pp. 527-528.

CAPILLARY TUBE HEMOGLOBINOMETER AND OXIMETER

A portion of the disclosure of this patent document contains material which is subject to copyright protection. The owner has no objection to the facsimile reproduction by anyone of the patent document or the patent disclosure, as it appears in the Patent and Trademark Office patent file or records, but otherwise reserves all rights whatsoever.

TECHNICAL FIELD

The invention relates to the measurement of total hemoglobin concentration and percentage of hemoglobin saturated with oxygen in whole, undiluted blood.

BACKGROUND OF THE INVENTION

Oximeters provide useful measurements of oxyhemoglobin saturation for clinical purposes and for physiological studies of oxygen transport. Unfortunately, presently available oximeters suffer from several serious disadvantages. They are often bulky, expensive instruments designed primarily for hospital use, and they can be particularly inaccurate in the low oxygen saturation range. In addition, known oximeters typically destroy the blood sample by diluting or hemolyzing it before measurement thereby rendering the blood sample useless for further study. Those oximeters that use whole, undiluted blood must be recalibrated if the total hemoglobin concentration changes.

SUMMARY OF THE INVENTION

The present invention avoids the disadvantages of prior art oximeters by first measuring the total hemoglobin concentration of a whole, undiluted blood sample, and then using the measured total hemoglobin concentration in computing the percent oxyhemoglobin. Thus, the present invention automatically compensates for any change in the total hemoglobin concentration, and remains calibrated despite fluctuations in the hematocrit or total hemoglobin content.

The oximeter of the present invention employs a unique optical design including a capillary tube holder which includes infrared and red light emitting diodes positioned relative to a photodetector so that the intensity of detected infrared light rises monotonically as total hemoglobin concentration decreases. The total hemoglobin concentration of a blood sample within the capillary tube is then calculated from infrared intensity. Then, using the measured value of total hemoglobin concentration, the percent oxyhemoglobin is calculated from the ratio of the logarithm of red light intensity to the logarithm of infrared light intensity. Additional nonlinearities are then corrected by applying a function which expresses actual percent oxyhemoglobin in terms of predicted percent oxyhemoglobin.

Measurements are preferably performed directly on a capillary tube commonly used to collect blood samples in many clinical settings.

Thus, the invention selectively illuminates an undiluted sample of whole blood contained in a capillary tube cuvette with infrared and red light, and detects the infrared and red light at a predetermiend measuring location along an axis of the cuvette. Then, total hemoglobin concentration is calculated as a first calibrated function of infrared intensity and percent oxyhemoglobin is calculated as a second calibrated function of the ratio of the logarithm of red light intensity to the logarithm of infrared light intensity, the second calibrated function being related to the calculated total hemoglobin concentration.

In addition, if dissolved oxygenis ignored, the invention can also accurately calculate total blood oxygen content as a function of total hemoglobin concentration and percent oxyhemoglobin.

DETAILED DESCRIPTION OF THE PREFERRED EMBODIMENT

Figure 1:
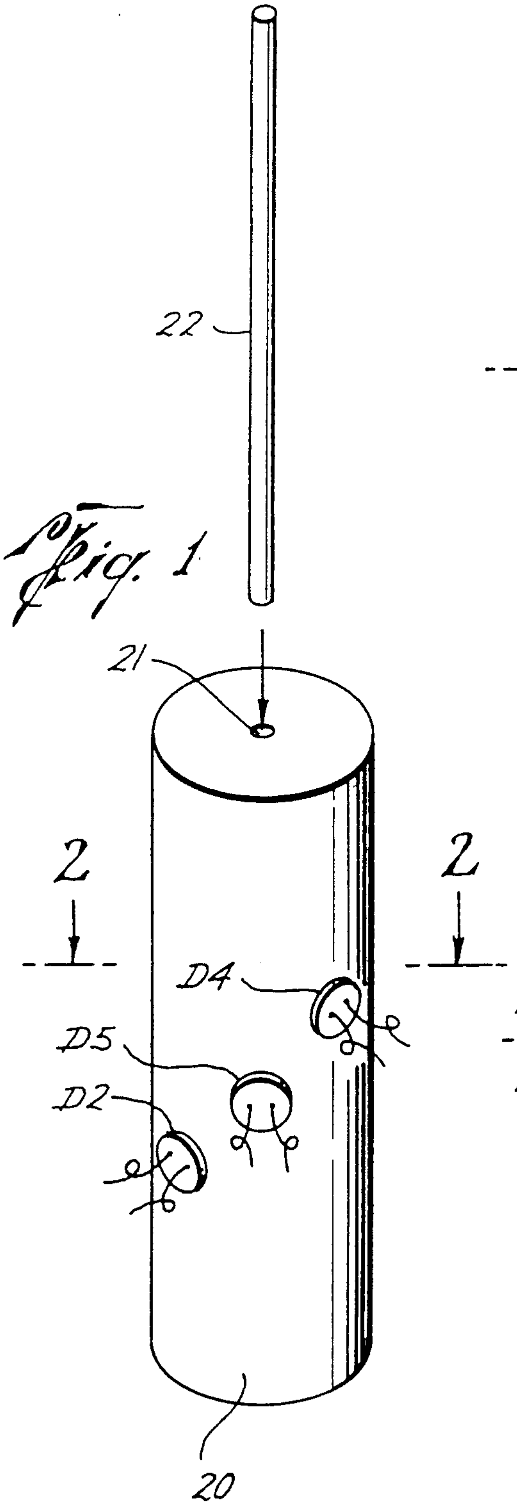
FIG. 1 is the capillary tube holder of the present invention showing the relative positions of the light emitters and detector.
Figure 2:
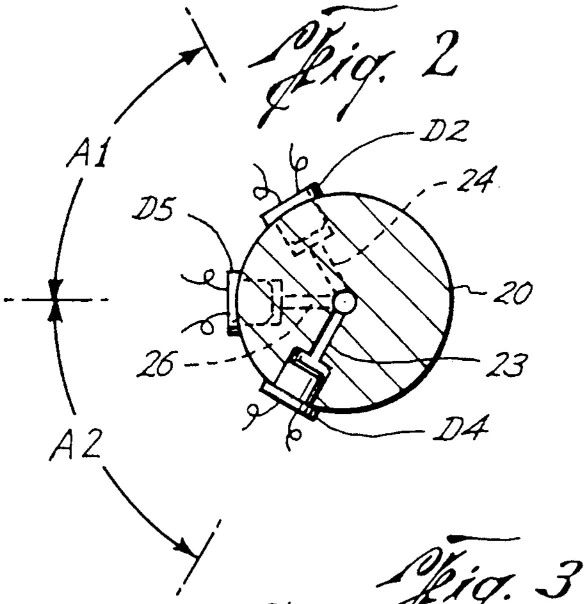
FIGS. 2 and 3 are sectional views taken through the capillary holder of FIG. 1.
Figure 3:
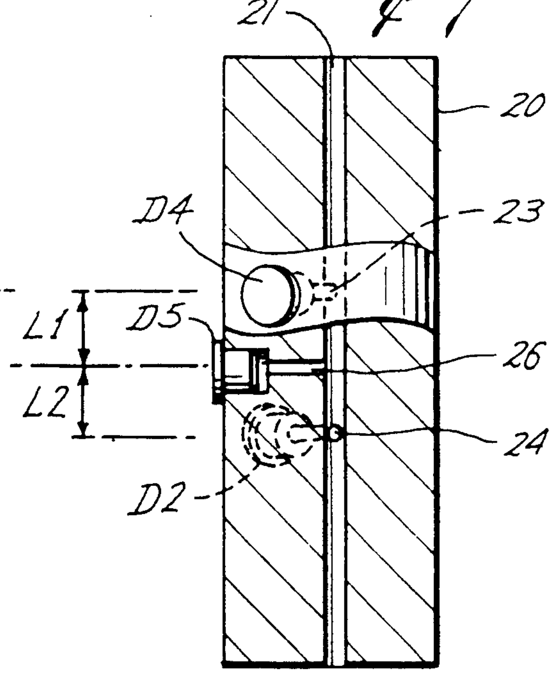

Referring to FIGS. 1-3, the optical configuration of the present invention is presented. Cylinder 20, preferably made of black phenolic, includes bore 21 drilled along the longitudinal axis of cylinder 20. Bore 21 accommodates glass capillary tube 22 which holds a whole, undiluted blood sample. Capillary tube 22 may be of the kind commonly used for microhematocrit determinations, for example, a Fisher Scientific type 02-668-66 capillary tube. Bore 21 has a diameter sufficient to accommodate capillary tube 22. Capillary tube 22 serves as an inexpensive, widely available cuvette. Holes 23 and 24 are drilled in cylinder 20 perpendicular to bore 21. Holes 23 and 24 guide light from light-emitting diodes D4 and D2, respectively, to illuminate blood cells contained within tube 22, positioned within bore 21. Light-emitting diode D2 preferably emits infrared light having a wavelength of approximately 800 nanometers, and light-emitting diode D4 preferably emits red light having a wavelength of approximately 660 nanometers. Hole 26 is also drilled in cylinder 20 perpendicular to bore 21 and directs light from bore 21 to photodetector D5. The diameter of each of holes 23, 24 and 26 is preferably one millimeter.

Distance L1 between the center of hole 26 and the center of hole 23 measured along the longitudinal axis of cylinder 20 is preferably two millimeters. Distance L2 between the center of hole 26 and the center of hole 24 measured along the longitudinal axis of cylinder 20 is also preferably two millimeters. Angle A1 between light-emitting diode D2 and photodetector D5 is preferably 60°, and angle A2 measured between light-emitting diode D4 and photodetector D5 is also preferably 60°.

These dimensions for the optical configuration of the present invention result in the intensity of infrared light being a monotonic function of total hemoglobin concentration of a whole undiluted blood sample contained within capillary tube 22, and avoids the parabolic functional dependence of known optical configurations.

Other optical configurations may be used in accordance with the present invention, so long as the detected intensity of infrared light is a monotonic function of total hemoglobin concentration of a whole blood sample contained within capillary tube 22.

Although FIGS. 1-3 show diodes D2 and D4 and photodetector D5 mounted directly within cavities in cylinder 20, diodes D2 and D4 and photodetector D5 may be coupled to cylinder 20 through fiber-opic light guides used to guide light to and from tube 22 within bore 21 of cylinder 20.

In operation, once capillary tube 22 is filled with a 25-70 microliter sample of whole, undiluted blood, one end of capillary tube 22 is sealed with a cap or clay, and tube 22 is inserted into bore 21 of cylinder 20 as shown in FIG. 1.

The blood in capillary tube 22 is then illuminated alternately with infrared and red light from light-emitting diodes D2 and D4, respectively. When either light-emitting diode is energized, light scattered by red blood cells in the blood sample travels two millimeters along the axis of capillary tube 22 where the light escapes through hole 26 and reaches photodetector D5. The timing and intensity of the energization of light-emitting diodes D2 and D4, and the calculations of total hemoglobin concentration and percent oxyhemoglobin are performed by the microprocessor-based circuitry shown in FIGS. 4 and 5.

Figure 4:
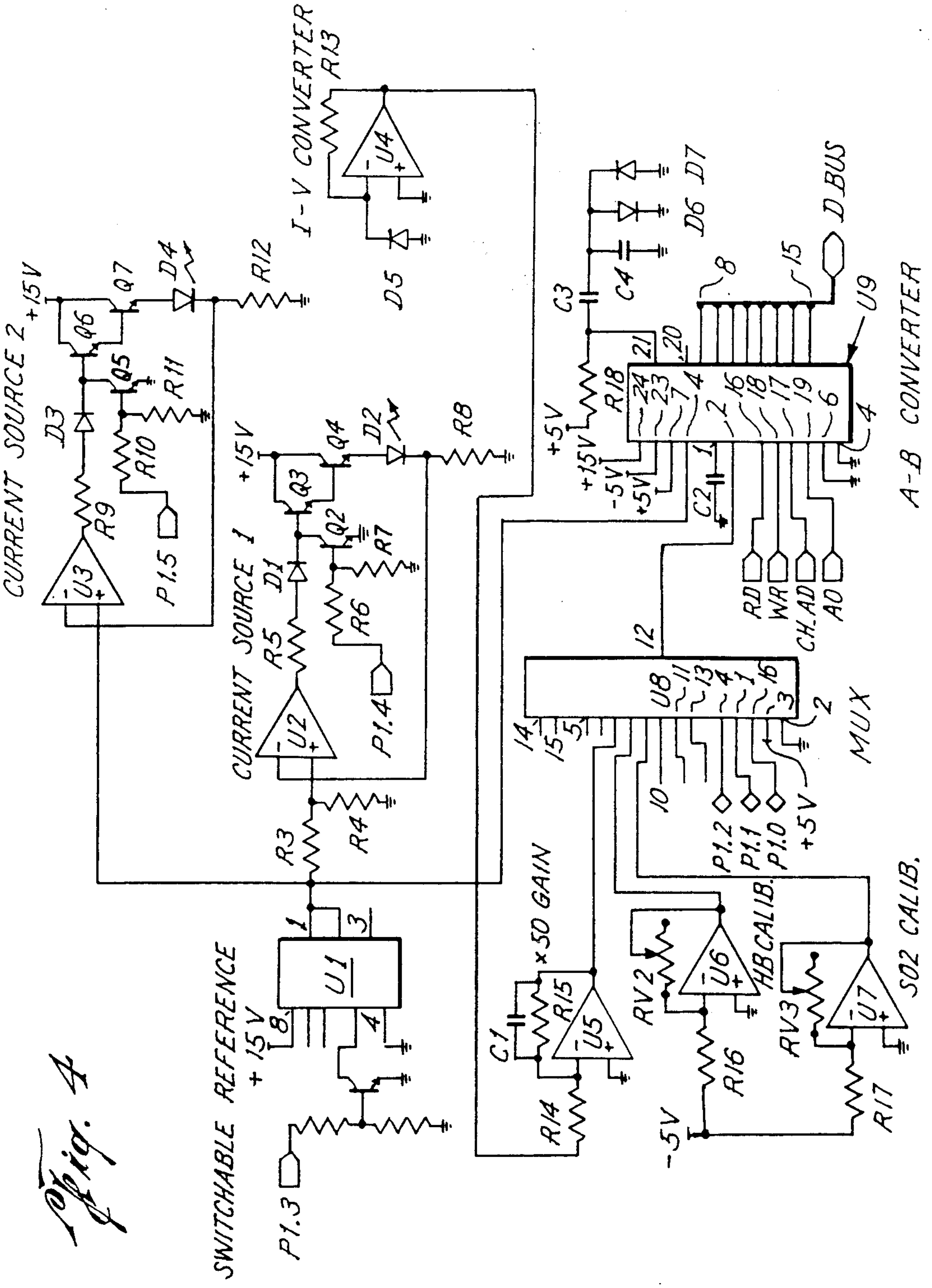
FIGS. 4 and 5 are a detailed electrical schematic of the present invention.
Figure 5:
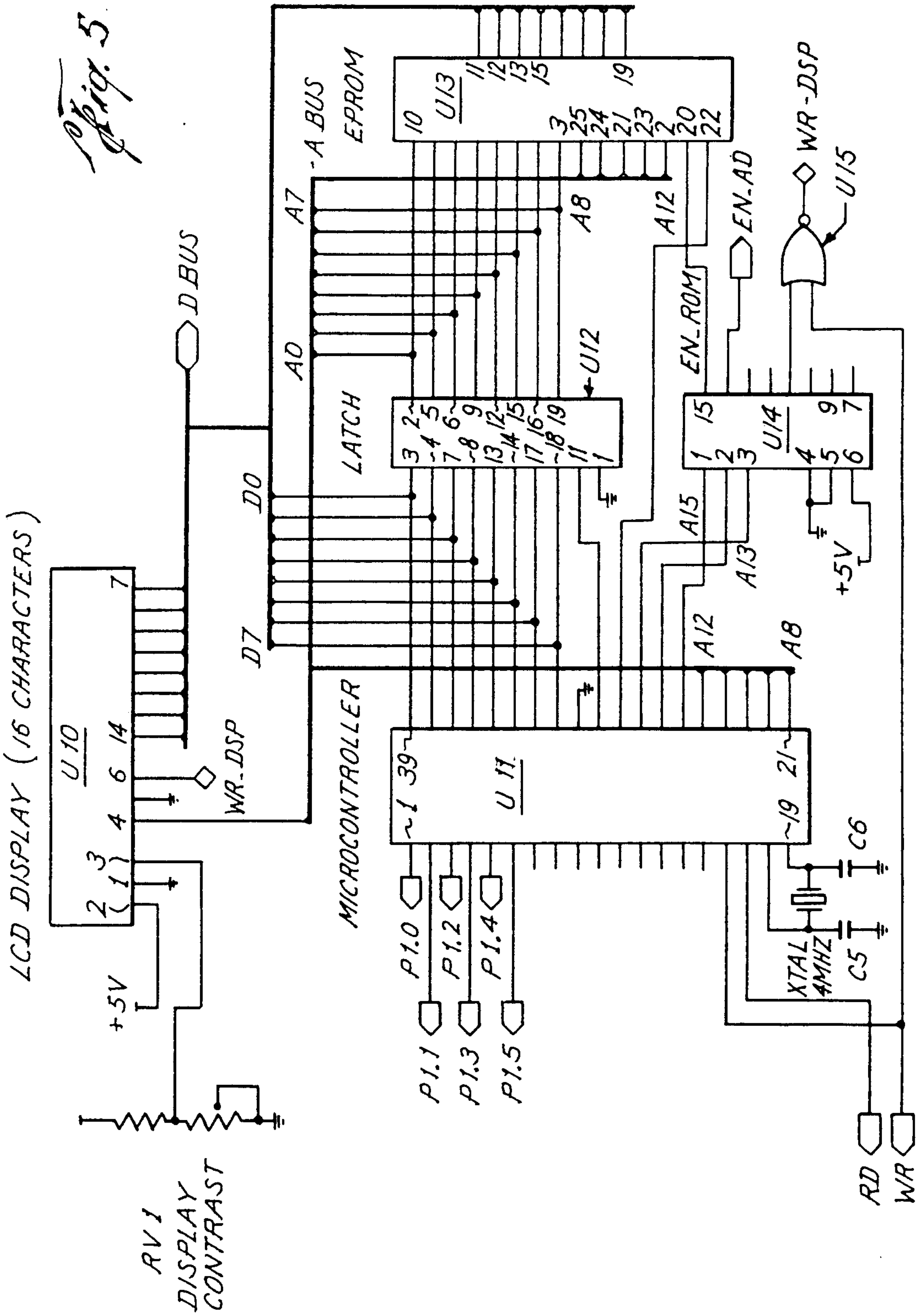

Referring to FIGS. 4 and 5, the electrical circuitry of the present invention is disclosed. The numbers adjacent the pins of integrated circuits U1-14 are the pin numbers of the preferred integrated circuits, listed in Table I.

Light-emitting diodes D2 and D4 are alternately energized under control of microprocessor U11. Specifically, switchable reference U1 is adjusted by microprocessor U11 using control line P1.3, connected through resistors R1, R2 and transistor Q1. The output of switchable reference U1 is applied to operational amplifiers U2 and U3 which control current applied to light-emitting diodes D2 and D4, respectively. The output of switchable reference U1 is connected to the noninverting input of operational amplifier U2 through resistive divider R3, R4. Operational amplifier U2 applies a constant current to light-emitting diode D2 through resistor R5, diode D1, and transistors Q3 and Q4. Negative feedback is provided to operational amplifier U2 by current-sensing resistor R8.

Similarly, the output of switchable reference U1 is connected to the noninverting input of operational amplifier U3. Operational amplifier U3 applies a constant current to light-emitting diode D4 through resistor R9, diode D3, and transistors Q6 and Q7. Negative feedback is provided to operational amplifier U3 by current-sensing resistor R12.

Light-emitting diodes D2 and D4 are alternatively energized under control of microprocessor U11 via control lines P1.4 and P1.5. Light-emitting diode D2 is turned on and off by microprocessor U11 through control line P1.4, resistors R6, R7 and transistor Q2. Light-emitting diode D4 is turned on and off by microprocessor U11 through control line P1.5, resistors R10, R11 and transistor Q5.

Thus, by varying the voltage supplied by switchable reference U1 through use of control line P1.3, and by alternately energizing light-emitting diodes D2 and D4 through control lines P1.4 and P1.5, microprocessor U11 controls the intensity and the timing of energization of light-emitting diodes D2 and D4.

Photodetector D5 is connected to current-voltage converter U4, including feedback resistor R13. The output of current-voltage converter U4 is connected to operational amplifier U5 configured as an inverting amplifier including resistors R14, R15 and capacitor C1. In the preferred embodiment, operational amplifier U15 provides a gain of 50. The output of operational amplifier U5 is provided as one of three inputs to analog multiplexer U8. The outputs of operational amplifiers U6 and U7 are also provided as inputs to analog multiplexer U8. Operational amplifier U6 is configured with resistor R16 and potentiometer RV2 to allow calibration of total hemoglobin concentration, (Hb), by adjustment of potentiometer RV2, as described in more detail below. Similarly, operational amplifier U7 is configured with resistor R17 and potentiometer RV3 to allow calibration of percent oxyhemoglobin (SO2) with adjustment of potentiometer RV3, as discussed in more detail below.

Analog multiplexer U8 is controlled by microprocessor U11 through control lines P1.0, P1.1 and P1.2 to select one of the three inputs for application to analog-to-digital (A-D) converter U9. A-D converter U9 is operated under the control of microprocessor U11 through read control line, RD, write control line WR, enable A-D control line, EN_AD, and address line A0. The output of A-D converter U9 is applied to 8-bit data bus, DBUS, which is connected to microprocessor U11. In the preferred embodiment, analog values sampled by A-D converter U9 are converted to a 12-bit digital number which is applied to 8-bit data bus, DBUS, over two clock cycles. Resistor R18, capacitors C3 and C4, and diodes D6 and D7 form an RC timing circuit for the clock circuit within A-D converter U9.

Also connected to microprocessor U11 are crystal, XTAL, with capacitors C5 and C6, which provide a 4 megaHertz clock for microprocessor U11, and address bus, ABUS. Data latch U12 is configured so as to allow the same outputs from microprocessor U11 to carry either data or address information. Read only memory (ROM) U13 stores a computer program for controlling the operation of the hardware of the present invention. The program is described in detail in connection with the flow chart of FIG. 11, which is a brief flow chart representation of the source code computer program included as a part of this specification. Address converter U14 converts addresses provided by microprocessor U11 into the enable ROM signal, EN_ROM, enable A-D signal, EN_AD, and along with NOR gate U15, generates write display signal, WR_DSP.

Display U10 is provided to display various measured blood parameters, including total hemoglobin and percent oxyhemoglobin. The contrast of display U10 is controlled by potentiometer RV1.

The particular components used in the present invention as disclosed in FIGS. 4 and 5 are listed in Table I, along with sources for such components, where appropriate. It should be noted that although the preferred infrared wavelength is 800 nm, readily available light-emitting diodes emit infrared at 813 nm, which has proven acceptable. The listing of these components should not be considered to be a limitation of the present invention but is offered for the purpose of illustration only.

TABLE I

| Designator | Component Type or Value | Source |
|---|---|---|
| U1 | AD584 | Analog Devices |
| U2, U3 | TL072A Op Amp | Motorola Semiconductor |
| U4 | AD547 Op Amp | Analog Devices |
| U5, U6, U7 | ADOP-07 Op Amp | Analog Devices |
| U8 | AD7501 Multiplexer | Analog Devices |
| U9 | AD7578 A-D Converter | Analog Devices |
| U10 | LM2020 LCD | Densitron Corp. |
| U11 | 8031 Microprocessor | Intel Corp. |
| U12 | 74LS373 Data Latch | Texas Instruments |
| U13 | 27C648K EPROM | Intel Corp. |
| U14 | 74LS138 Decoder | Texas Instruments |
| U15 | 74LS02 NOR | Texas Instruments |
| Q1-7 | 2N3904 Transistor | Motorola Semiconductor |
| D1, D3, D6 D7 | 1N4148 Diode | General Electric |
| D2 | MFOE1200, or MLED 76 LED (813 nm, IR) | Motorola Semiconductor |
| D4 | F511 LED (660 nm, R), or MLED 76 (660 nm, R) | AC Interface, Inc. Motorola Semiconductor |
| D5 | PIN-3DP Photodiode | United Detector Technology |
| RV1 | 50K Potentiometer | |
| RV2, RV3 | 10K Potentiometer | |
| R1, R2, R6, R7, R10, R11, R16, R17 | 10K Ohms | |
| R3, R4 | 11.5K Ohms | |
| R5, R9 | 100K Ohms | |
| R8, R12 | 50 Ohms | |
| R13 | 1M Ohms | |
| R14 | 1K Ohms | |
| R15 | 50K Ohms | |
| R18 | 56K Ohms | |
| C1 | 2 nF | |
| C2 | 2.2 nF | |
| C3 | 3.9 nF | |
| C4 | 560 pF | |
| C5, C6 | 22 pF | |
| XTAL | 4 MHz Crystal | |

In order to develop and evaluate the present invention, whole, undiluted blood was centrifuged and the red blood cells and plasma were combined into various known proportions to produce a range of total hemoglobin concentrations, (Hb). To measure total hemoglobin concentration independently, the hemoglobin concentrations of hemolyzed, oxygenated aliquots were measured on a refractometer or on an Instrumentation Laboratories Model 482 oximeter. To study the relationships between percent oxyhemoglobin saturation, SO2, and the transmitted light intensities, blood of a fixed hemoglobin concentration was tonometered with mixtures of 5% $CO_2$ and various proportions of oxygen. The oxygen contents of aliquots of the blood were analyzed using an Instrumentation Laboratories Model 482 oximeter, and the optical transmittance of the aliquots of the blood were measured using the red and infrared wavelengths of the present invention. Percent oxyhemoglobin saturation, SO2, was determined with the Instrumentation Laboratories Model 482 oximeter.

Figure 6:
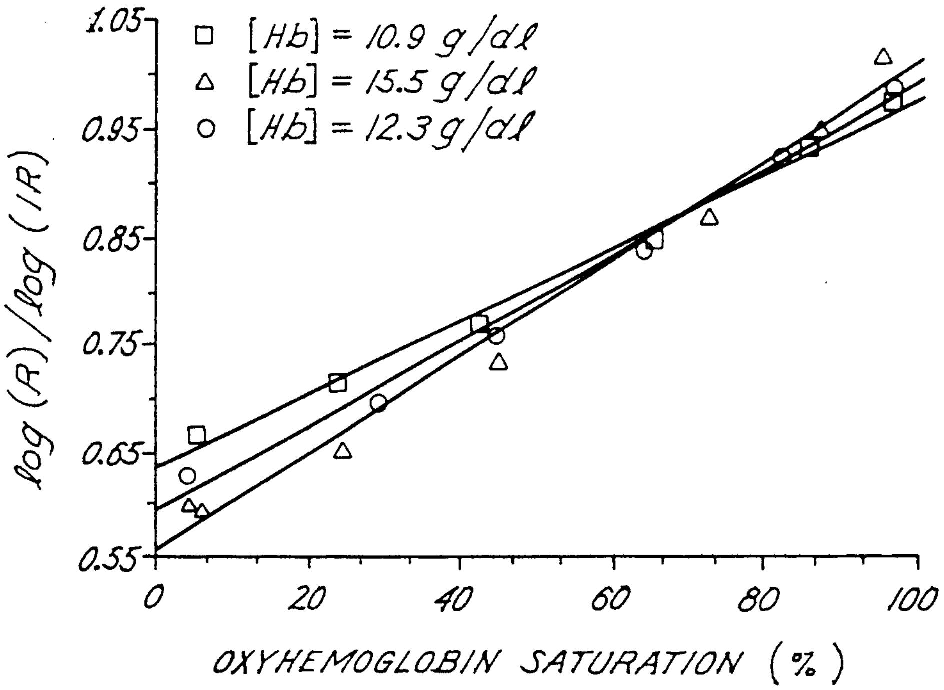
FIG. 6 is a graph showing the ratio of the logarithms of the intensity of red to infrared light for various hemoglobin concentrations as a function of oxyhemoglobin saturation.

In terms of raw data, a calibration curve of an oximeter includes the relationship between percent oxyhemoglobin saturation, SO2, and the ratio of optical reflectances or absorbances at two appropriate light wavelengths, for example, red and infrared. FIG. 6 shows this relationship for the wavelengths used in the present invention (660 and 800nm), and demonstrates the known dependence of the calibration curves on total hemoglobin concentration, (Hb). Blood with three different hemoglobin concentrations yields three distinct curves relating the logarithm ratios of red and infrared intensity to oxyhemoglobin saturation, SO2. According to the present invention, this dependence is corrected for by correcting for changes in total hemoglobin concentration, (Hb).

Figure 7:
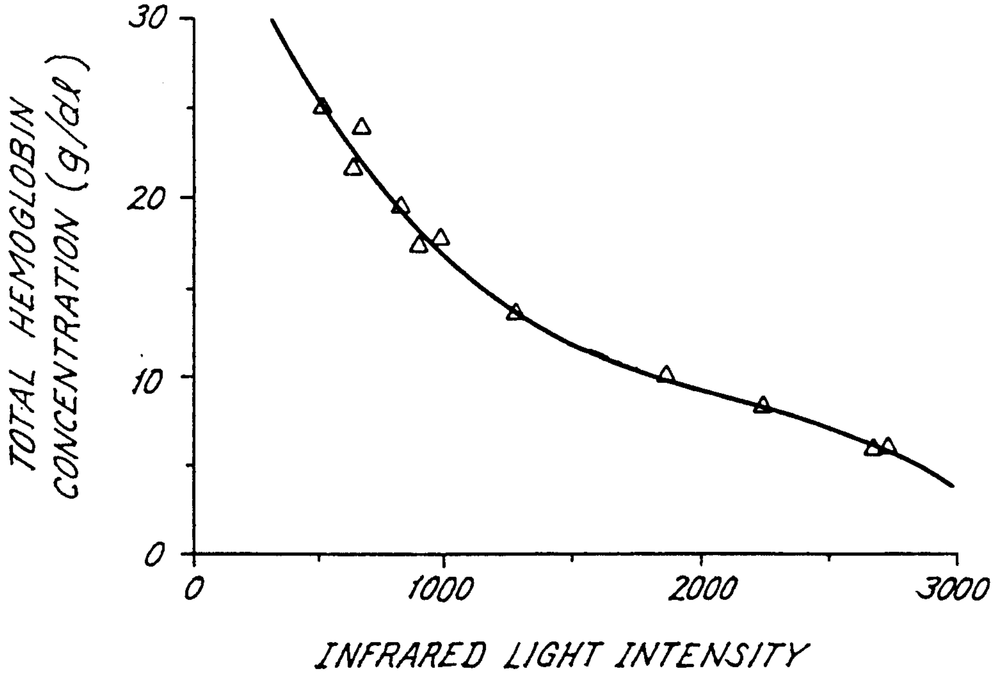
FIG. 7 is a graph of total hemoglobin concentration as a function of infrared light intensity.

Total hemoglobin concentration is determined, according to the present invention, by using the above-described unique optical geometry (FIGS. 1-3) to cause the intensity of infrared light to rise monotonically as total hemoglobin concentration, (Hb), decreases. FIG. 7 is a graph of this monotonic relationship. Total hemoglobin concentration is plotted on the Y-axis, and infrared intensity is plotted on the X-axis. The units of infrared intensity are in terms of the output of A-D converter U9 which linearly converts a voltage signal of from 0-5 Volts into a 12-bit binary number of from 0-4095 (in decimal). The monotonic relationship existing between total hemoglobin concentration, (Hb), and infrared light intensity, IR, can generally be represented as a polynomial function of the form:

$$(Hb)=A_0+A_1\,IR+\ldots+A_nIR^n \qquad (1)$$

where n is an integer greater than or equal to 2, and $A_0$, $A_1$, ..., $A_n$ are calibration constants determined to fit the monotonic curve of FIG. 7. In the preferred embodiment, $n=3$, $A_0=39.935$, $A_1=-3.5255\times10^{-2}$, $A_2=1.4398\times10^{-5}$, and $A_3=-2.2244\times10^{-9}$.

Figure 8:
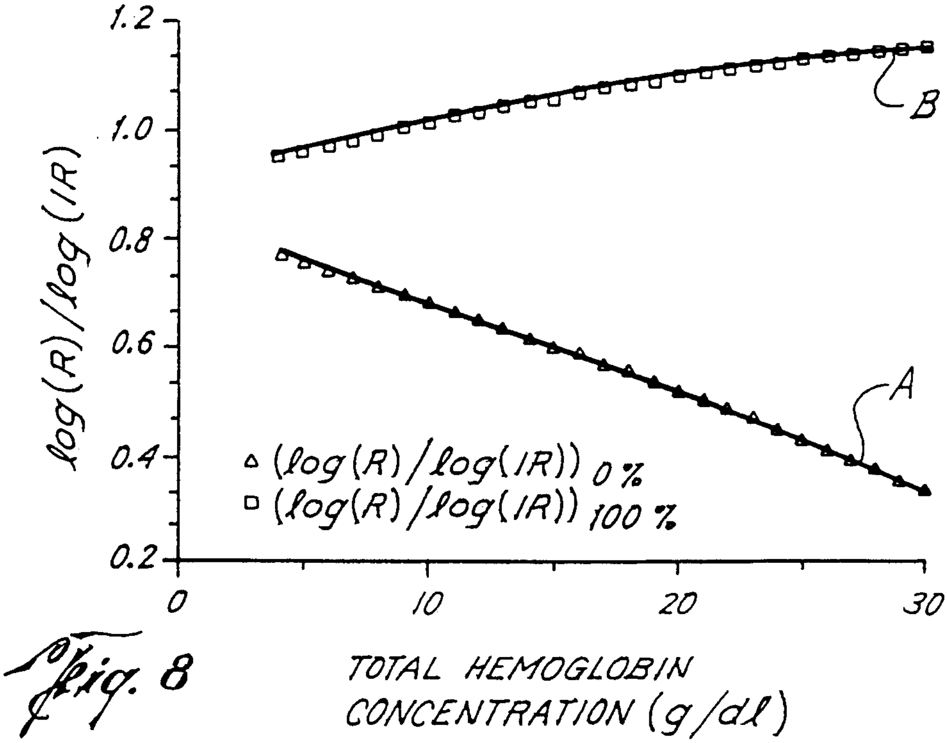
FIG. 8 is a graph showing the ratio of the logarithms of red to infrared light intensity for oxygenated and deoxygenated blood as functions of total hemoglobin concentration.

With this mathematical relationship relating total hemoglobin concentration, (Hb), to infrared intensity, IR, the calculation of oxyhemoglobin saturation, SO2, is then computed. To accomplish this, curves were fit to data to obtain empirical equations describing the LogR/LogIR ratios for oxygenated and deoxygenated blood as functions of the total hemoglobin concentration, (Hb). In FIG. 8, curve A is the curve for deoxygenated blood, and relates the LogR/LogIR ratio to total hemoglobin concentration for deoxygenated blood, and curve B in FIG. 8 relates the LogR/LogIR ratio to total hemoglobin concentration, (Hb), for fully oxygenated blood. In the preferred embodiment, the polynomial equation relating LogR/LogIR ratio to total hemoglobin concentration, (Hb), for deoxygenated blood can generally be represented as a polynomial function of the form:

$$(LogR/LogIR)_{0\%}=C_0+C_1(Hb)+\ldots+C_n(Hb)^n \qquad (2)$$

where n is an integer greater than or equal to 2, and $C_0$, $C_1$, ..., $C_n$ are calibration constants determined to fit the deoxygenated curve of FIG. 8. In the preferred embodiment, $n=3$, $C_0=0.83862$, $C_1=-1.68\times10^{-2}$, $C_2=1.0658\times10^{-4}$ and $C_3=-3.8543\times10^{-6}$.

Curve B which relates the LogR/LogIR ratio to total hemoglobin concentration, (Hb), for oxygenated blood can also generally be represented as a polynomial function of the form:

$$(LogR/LogIR)_{100\%}=D_0+D_1(Hb)+\ldots+D_n(Hb)^n \qquad (3)$$

where n is an integer greater than or equal to 2 and $D_0$, $D_1$, ., $D_n$ are calibration constants determined to fit the oxygenated curve of FIG. 8. In the preferred embodiment, $n=3$, $D_0=0.91001$, $D_1=1.0913\times10^{-2}$, $D_2=-5.4506\times10^{-5}$ and $D_3=-1.5164\times10^{-6}$.

The polynomial functions describing deoxygenated curve A and oxygenated curve B are then used in combination with the total hemoglobin concentration, (Hb), calculated from equation (1), to compute the appropriate oximeter curve end-points. A first estimate of oxyhemoglobin saturation is then calculated using the linear equation:

$$SO2 = 100\frac{((LogR/LogIR) - (LogR/LogIR)_{0\%})}{((LogR/LogIR)_{100\%} - (LogR/LogIR)_{0\%})} \quad (4)$$

where $(LogR/LogIR)_{0\%}$ is the ratio of the logarithm of red light intensity to the logarithm of infrared light intensity for 0% saturated blood (deoxygenated) at the calculated (Hb), and $(LogR/LogIR)_{100\%}$ is the logarithm of red light intensity divided by the logarithm of infrared light intensity for 100% oxygen saturated blood (oxygenated) at the calculated (Hb).

Figure 9:
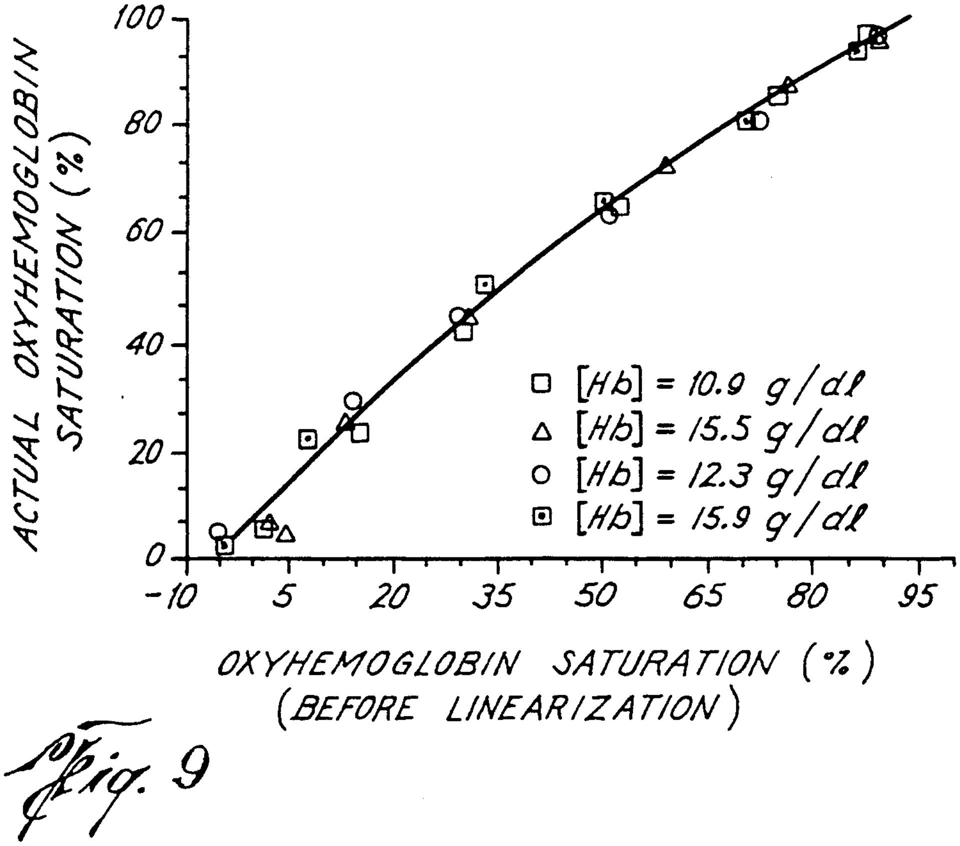
FIG. 9 is a graph of actual percent oxyhemoglobin versus percent oxyhemoglobin using the present invention after calibration but before linearization.

Using this method, predicted percent oxyhemoglobin, SO2, was calculated and was compared with independently measured oxyhemoglobin saturation using an Instrumentation Laboratories Model 482 oximeter, and is plotted in FIG. 9. As can be seen, although there is complete correction for varying total hemoglobin concentration, (Hb), there exists a slight nonlinearity in the predicted oxyhemoglobin calculations versus the independently measured oxyhemoglobin calculations.

Therefore, the last step according to the present invention is to linearize the instrument's calculation by using a function which expresses the independently measured percent oxyhemoglobin saturation as a function of the uncorrected measured percent oxyhemoglobin saturation. Once again, this equation is a polynomial of the form:

$$(SO2)_{corrected}=B_0+B_1(SO2)+\ldots+B_n(SO2)^n \quad (5)$$

where $(SO2)_{corrected}$ is the corrected percent oxygen saturation, n is an integer greater than or equal to 2, and $B_0, B_1, \ldots, B_n$ are calibration constants determined by curve fitting. In the preferred embodiment, $n=3$, $B_0=6.3825$, $B_1=1.3877$, $B_2=-5.0275\times10^{-3}$ and $B_3=9.0821\times10^{-6}$.

Figure 10:
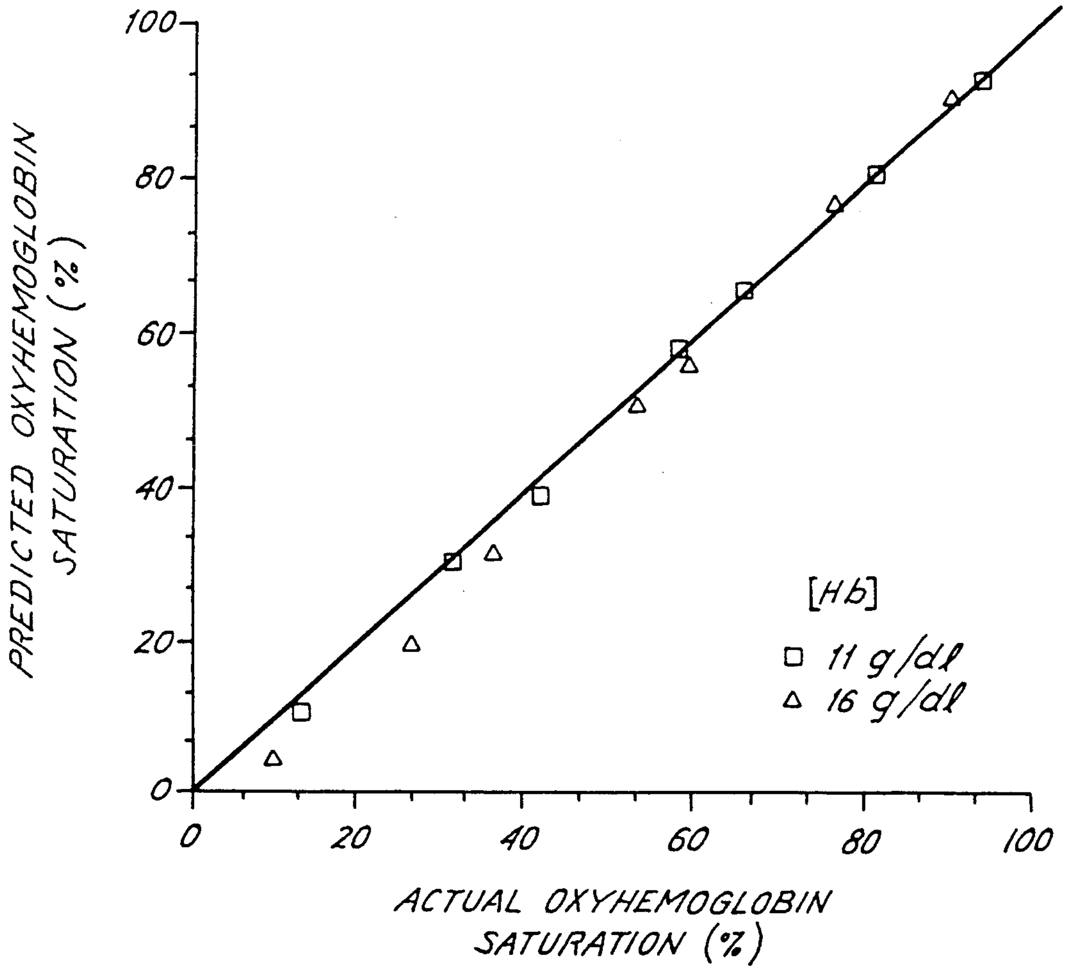
FIG. 10 is a graph showing percent oxyhemoglobin measured by the present invention after linearization as a function of actual percent oxygen saturation.

FIG. 10 shows the percent oxyhemoglobin saturation measured by the oximeter of the present invention when properly calibrated and corrected, versus percent oxyhemoglobin saturation measured independently using an Instrumentation Laboratories Model 482 oximeter. FIG. 10 illustrates percent oxyhemoglobin saturation measurements for both high and low hemoglobin concentrations.

If dissolved oxygen is ignored, the present invention can also be used to calculate total blood oxygen content, $O_2$, from the equation:

$$O_2=(Hb)\times1.34\times(SO2/100)$$

where 1.34 is the number of milliliters of oxygen carried by one gram of hemoglobin.

The accuracy of the present invention compared with known hemoglobinometers and oximeters is summarized in Table II.

TABLE II

| Measured Quantity | Units | Range | Accuracy |
|---|---|---|---|
| (Hb) | g Hb/dl | 5-30 | 0.63 |
| SO2 | % | 0-100 | 2.35 |
| $O_2$ | ml $O_2$/dl | 0-40 | 0.79 |

The accuracies of percent oxyhemoglobin concentration and blood oxygen content are RMS errors when compared with an Instrumentation Laboratories Model 482 oximeter over 13 measurements. The accuracy of total hemoglobin concentration is an RMS error when compared with an Instrumentation Laboratories Model 482 oximeter over 8 measurements.

Figure 11:
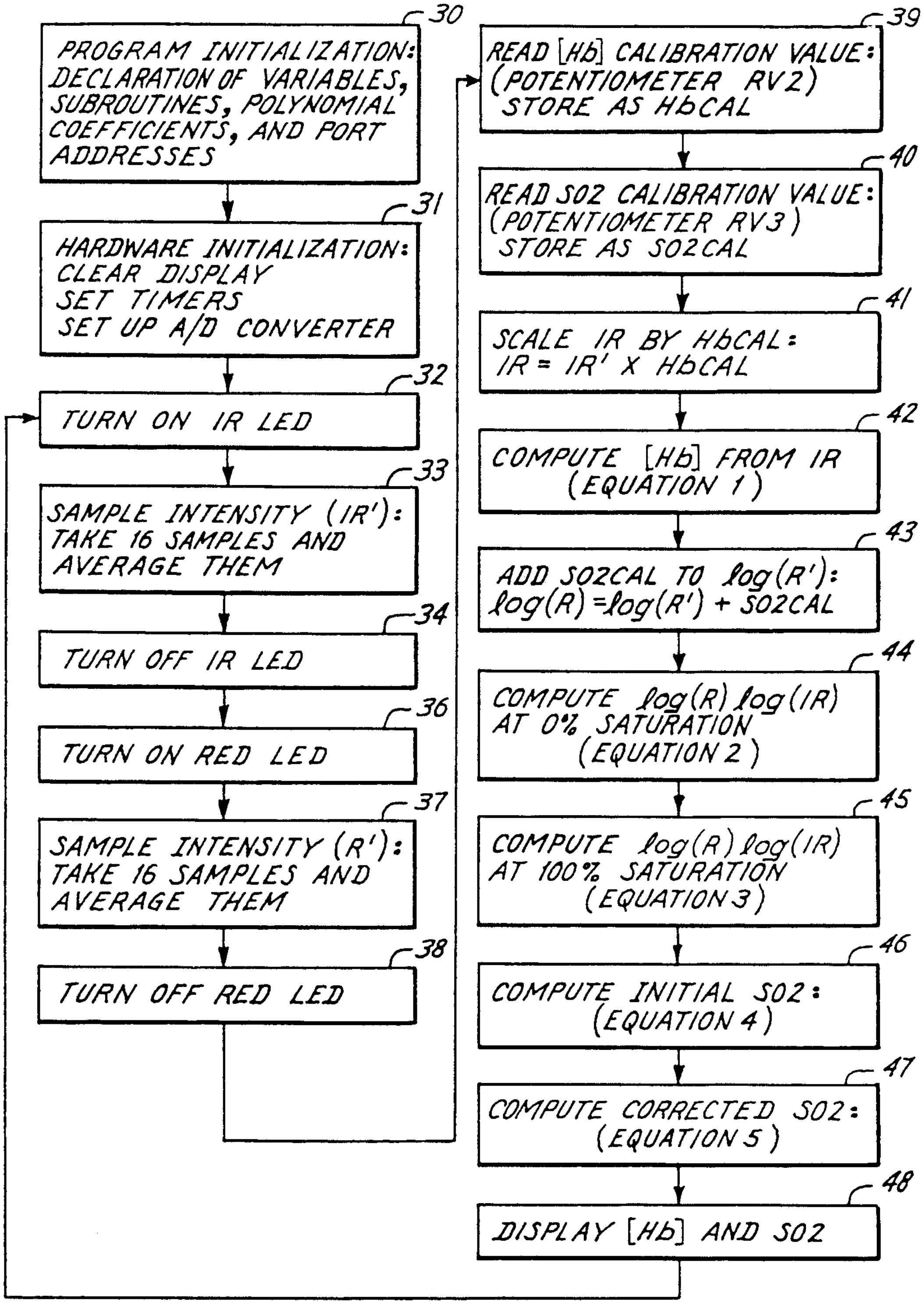
FIG. 11 is a flow chart of the processing steps of the microprocessor of FIG. 5, according to the present invention.

Referring to FIG. 11, the flow of control of microprocessor U11 of FIG. 5 is described in order to accomplish the above operation. Before cyclic processing is begun, the present invention is calibrated by adjustment of potentiometers RV2 and RV3 (FIG. 4) while measuring a blood sample of known hemoglobin concentration and percent oxygen saturation. Potentiometers RV2 and RV3 are adjusted to produce analog voltages which are converted into 12-bit digital numbers by A-D converter U9 and applied to microprocessor U11 for application to display U10. The digitized calibration quantities are then used to calculate hemoglobin concentration calibration parameter, HbCAL, and percent oxygen saturation calibration constant, SO2CAL, using the following equations:

$$HbCAL=0.5+(\text{digitized } RV2 \text{ voltage})/3920$$

$$SO2CAL=-0.5+(\text{digitized } RV3 \text{ voltage})/3800$$

It should be emphasized that once calibrated, the present invention need not be recalibrated to accommodate changing hemoglobin concentrations or percent oxygen saturation. Calibration need be performed only periodically in order to accommodate instrument changes unrelated to the sample, for example, changing light intensity, dust accumulation, and the like.

Referring to the flow chart of FIG. 11, after calibration the program is initialized in block 30 including declaring the initial states of variables and the coefficients of equations 1-5. Next, in block 31, the hardware is initialized. For example, the display is cleared, and A-D converter U9 is initialized.

Control then passes to block 32 which begins cyclic operation. In block 32, the infrared LED D2 is turned on. Then, in block 33, 16 samples are taken from photodetector D5, and are averaged to produce unscaled infrared intensity, IR'. In block 34, infrared diode D2 is turned off. Similarly, in block 36, red LED D4 is turned on, unscaled red intensity value, R', is calculated in block 37 as an average of 16 samples from photodetector D5 and in block 38, red LED D4 is turned off.

Control then passes to blocks 39 and 40 wherein hemoglobin calibration parameter, HbCAL, and percent oxygen saturation calibration parameter, SO2CAL, set by potentiometers RV2 and RV3, respectively, are read and stored.

Then, in block 41, unscaled infrared intensity, IR', is scaled by multiplying by hemoglobin concentration calibration parameter, HbCAL, to produce scaled infrared intensity, IR. In block 42, total hemoglobin concentration, (Hb), is calculated from scaled infrared intensity, IR, using equation (1) above.

Control then passes to block 43 where the logarithm of unscaled red intensity, LogR', is calibrated by adding to percent oxygen saturation calibration parameter, SO2CAL, to produce the logarithm of scaled red intensity, LogR.

Then, in blocks 44 and 45, equations (2) and (3) are used to calculate the ratio of the logarithm of scaled red intensity to the logarithm of infrared intensity for 0% oxygen saturation and for 100% oxygen saturation, respectively. In block 46, initial percent oxygen saturation is calculated using equation (4), and in bock 47, corrected percent oxygen saturation is calculated using equation (5).

Finally, in block 48, total hemoglobin concentration, (Hb), and corrected percent oxygen saturation, SO2, are displayed. Control then returns to block 32 where processing continues in a cyclic manner.

The following is a source code listing of the computer program used in the present invention written in the assembly language of the preferred 8031 microprocessor. The flow chart of FIG. 11 summarizes this computer program.

COPYRIGHT 1989,
BOARD OF REGENTS, THE UNIVERSITY OF TEXAS SYSTEM

LINE SOURCE

```
$TITLE(PHI4: PHI Hb Oximeter)  DATE(28-Apr-88)
        NAME    PHI4            ; PHI4.A51

;  Last revision:  28 Apr 1988
;
;Accompanies a joint research publication entitled:
;       An Optical Hemoglobinometer for Whole Blood.
;
;Publication authored by:
;       J.L. Schmalzel, J.M. Steinke, V.T. Randal, and A.P. Shepherd
;
;       Department of Physiology
;       University of Texas Health Science Center
;       San Antonio, Texas 78284
;               and
;       Division of Engineering
;       University of Texas
;       San Antonio, Texas 78255

        EXTRN   CODE(CDLY)      ; delay >15 ms for display
        EXTRN   CODE(DDLY)      ; delay >50 us for data sent to display
        EXTRN   CODE(FIVE)      ; delay for approx. 5 secs. to allow testing
        EXTRN   CODE(LOADA)     ; update D/A w/ value passed via A
        EXTRN   CODE(CLRDSP)    ; clear display to clear/home position
        EXTRN   CODE(WRITE)     ; write message to LCD display
        EXTRN   CODE(WRITEA)    ; write single byte to LCD display
        EXTRN   CODE(JBD)       ; convert 12-bit binary to 5-digit BCD
        EXTRN   CODE(WRITED)    ; display 4 digits to line 2 of display
        EXTRN   CODE(SCALE)     ; scale raw A/D value by 1.221 mV/step
        EXTRN   CODE(ACDHI)     ; convert result from SCALE to proper BCD value
        EXTRN   CODE(ADDS1)     ; form 5-dig partial sum for V conversion
        EXTRN   CODE(ADDS2)     ; form 5-dig bcd sum for quad. conv. in FP2-FP0
        EXTRN   CODE(WRITEV)    ; display 4 digits of V of form "X.XXX V"
        EXTRN   CODE(TAKE16)    ; take 16 samples in one 60 Hz period and ave.
        EXTRN   CODE(HEXOUT)    ; output contents of R1,R0 as 4 hex characters
        EXTRN   CODE(READAD)    ; perform an A/D conversion (results in R1,R0)
        EXTRN   CODE(ONE)       ; delay for 1 second
        EXTRN   CODE(WRTFP)     ; WRITE ASCII TO DISPLAY

        EXTRN   CODE(FPADD)     ; Basic Floating Point Operations (Single)
        EXTRN   CODE(FPMUL)
        EXTRN   CODE(FPDIV)
        EXTRN   CODE(FPADJY)
        EXTRN   CODE(FPCMP)
;
        EXTRN   CODE(AINT)
        EXTRN   CODE(FLOAT)
        EXTRN   CODE(INT)
;
        EXTRN   CODE(LDFAC)
```

```
LOC  OBJ          SOURCE
                          EXTRN   CODE(STFAC)
                  ;
                          EXTRN   CODE(DPTADD)
                          EXTRN   CODE(DPTSUB)
                  ;
                          EXTRN   CODE(FPEXP)      ; Floating Point Functions (single)
                          EXTRN   CODE(FPLOG)
                          EXTRN   CODE(FPLN)
                          EXTRN   CODE(FPXTOI)
                          EXTRN   CODE(FPSQRT)
                          EXTRN   CODE(FPCOS)
                          EXTRN   CODE(FPSIN)
                          EXTRN   CODE(FPTAN)
                          EXTRN   CODE(FPATN)
                          EXTRN   CODE(XSER)
                          EXTRN   CODE(XXSER)
                  ;
                          EXTRN   CODE(BINASC)     ; Floating Point Conversions (single)
                          EXTRN   CODE(ASCBIN)
                  ;
                  ;Begin program initialization
                  ;ADDRESS ASSIGNMENTS:
                  ;
                  ;               0000H-1FFFH  EPROM
                  ;               2000H-3FFFH  A/D
                  ;                  write to 2000H will start conversion
                  ;                  read from 2000H will read low byte
                  ;                  read from 2001H will read upper byte
                  ;                   note that lower nibble is data
                  ;               4000H-5FFFH  D/A-1
                  ;                  write to 4001H will latch data in input latch
                  ;               6000H-7FFFH  D/A-2
                  ;                  write to 6000H will load data from input latch
                  ;                  to output (D/A) latch
                  ;               8000H-9FFFH  DISPLAY (8000:COMMAND, 8001:DATA)
                  ;               A000H-BFFFH  8255 (A000:A, A001:B, A002:C, A003:CON)
                  ;               C000H-DFFFH  Static RAM at 0C000H
                  ;               E000H-FFFFH  <unassigned>
                  ;
                  ;XDATA ASSIGNMENTS FOR ABOVE EXTERNAL ADDRESSES:
                  ;
                          PUBLIC  PORTC,PORTB,PORTA,CSR,ADLOW,ADHI,DSPDAT,DSPCOM,DA1,DA2

A002              PORTC           XDATA   0A002H
A001              PORTB           XDATA   0A001H
A000              PORTA           XDATA   0A000H
A003              CSR             XDATA   0A003H
2000              ADLOW           XDATA   02000H
2001              ADHI            XDATA   02001H
8001              DSPDAT          XDATA   08001H
8000              DSPCOM          XDATA   08000H
4001              DA1             XDATA   04001H
6000              DA2             XDATA   06000H
                  ;
                  ;DATA ASSIGNMENTS (so register may be referred to by name with
                  ;               instructions requiring direct address--e.g., PUSH)
                  ;BANK 0 addresses for R0-R7:
                  ;
                          PUBLIC  BOR0,BOR1,BOR2,BOR3,BOR4,BOR5,BOR6,BOR7
```

```
0000              BOR0            DATA    00H
0001              BOR1            DATA    01H
0002              BOR2            DATA    02H
0003              BOR3            DATA    03H
0004              BOR4            DATA    04H
0005              BOR5            DATA    05H
0006              BOR6            DATA    06H
0007              BOR7            DATA    07H
                  ;
                  ;EQUATES:
                  ;
00FE              TCHI            EQU             0FEH    ;TIMERO coeffs.
00C0              TOLOW           EQU             0C0H
                  ;
                  ;PORT ASSIGNMENTS:
                  ;
                  ;                       P1.0            MUX address line LSB
                  ;                       P1.1              "
                  ;                       P1.2              "         MSB
                  ;                       P1.3            VREF STROBE ('1'=OFF, '0'=ON)
                  ;                       P1.4            Variable Current Source ('1'=OFF, '0'=ON)
                  ;                       P1.5            Fixed Current Source ('1'=OFF, '0'=ON)
                  ;                       P1.6            <unassigned>
                  ;                       P1.7            STATUS LED ('1'=ON, '0'=OFF)
                  ;
                  ;
                  ;
                  ;
                  ;=============== Start of FPAC variable declaractions ===============
                  ;  * * * * *
                  ;
                  ;  Floating Point Accumulator and Bit Flag Definitions
                  ;
                  ;  * * * * *
                  ;
                  ; ********** DIRECT BIT DECLARATIONS
                  ;
DBRSEG            SEGMENT DATA BITADDRESSABLE     ; Direct bit addressable address
                  RSEG    DBRSEG
                  ;
                  PUBLIC  FACBIT
                  PUBLIC  FACSGN,FACBTM,FACRNM,NANFLG,OVFFLG,UNFFLG
                  ;
0000              FACBIT: DS      1               ; Required byte
0007              FACSGN  BIT     FACBIT.7        ; Sign of value in FAC
0006              FACBTM  BIT     FACBIT.6        ; Bit temporary
0005              FACRNM  BIT     FACBIT.5        ; Flag to signal ROM resident constant
0004              NANFLG  BIT     FACBIT.4        ; Not-A-Number Result Flag
0003              OVFFLG  BIT     FACBIT.3        ; Overflow (Infinite) Result Flag
0002              UNFFLG  BIT     FACBIT.2        ; Underflow Result Flag
                  ; ***  FACBIT bits 1:0 hold error code (0, 1, 2, 3)  ***
                  ;
                  PUBLIC  DPFLAG,SIGFLG,MANSGN
                  PUBLIC  FNCSGN,FNCSEC
                  ;
0001              CNVBIT: DS      1
000F              DPFLAG  BIT     CNVBIT.7        ; Decimal point encountered flag
000E              SIGFLG  BIT     CNVBIT.6        ; Digits in mantissa encountered flag
000D              MANSGN  BIT     CNVBIT.5        ; Sign of number
                  ;
0009              FNCSGN  BIT     CNVBIT.1        ; Temporary sign bit
0009              FNCSEC  BIT     CNVBIT.0        ; Special post processing flag
                  ;
```

```
             ; **********  DIRECT BYTE DECLARATIONS
             ;
             DRSEG    SEGMENT DATA              ; Base of Direct byte temporaries
----                  RSEG     DRSEG
             ;
                      PUBLIC   FACTMP,FACEXP,FACMAN,EXPVLA
             ;
0000                  DS       5                ; Temporary mantissa
0005         FACTMP:  DS       1
             ;
0006                  DS       1                ; Floating Point Accumulator Exponent
0007         FACEXP:  DS       1
             ;
0008                  DS       5                ; Floating Point Accumulator Mantissa
000D         FACMAN:  DS       1
             ;
000E         EXPVLA:  DS       1                ; Required for conversion routines only
             ;
             ; **********  EXTERNAL MEMORY DECLARATIONS
             ;
             XDRSEG   SEGMENT XDATA
----                  RSEG     XDRSEG
             ;
0000         ASC_RAM_INFRARED_DATA:             DS      16
0010         ASC_RAM_RED_DATA:                  DS      16

0020         ASC_RAM_HB:                        DS      16
0030         ASC_RAM_SO2:                       DS      16

0040         ASC_RAM_HB_CAL:                    DS      16
0050         ASC_RAM_SO2_CAL:                   DS      16
0060         ASC_RAM_LOG_RATIO:                 DS      16
0070         ASC_RAM_OXY_END_POINT:             DS      16
0080         ASC_RAM_DEOXY_END_POINT:           DS      16

0090                                            DS      3
0093         BIN_RAM_INFRARED_DATA:             DS      1
0094                                            DS      1
0097         BIN_RAM_RED_DATA:                  DS      1
0098                                            DS      1
0099         BIN_RAM_HB:                        DS      1
009C                                            DS      1
009F         BIN_RAM_SO2:                       DS      1
00A0                                            DS      1
00A3         BIN_RAM_HB_CAL:                    DS      1
00A4                                            DS      1
00A7         BIN_RAM_SO2_CAL:                   DS      1
00A8                                            DS      1
00AB         BIN_RAM_LOG_RATIO:                 DS      1
00AC                                            DS      1
00AF         BIN_RAM_OXY_END_POINT:             DS      1
00B0                                            DS      1
00B3         BIN_RAM_DEOXY_END_POINT:           DS      1

00B4         INFRARED_LO_BYTE:  DS   1          ; Raw A/D values
00B5         INFRARED_HI_BYTE:  DS   1
00B6         RED_LO_BYTE:       DS   1
00B7         RED_HI_BYTE:       DS   1

00B8         HB_CAL_LO_BYTE:    DS   1
00B9         HB_CAL_HI_BYTE:    DS   1
00BA         SO2_CAL_LO_BYTE:   DS   1
00BB         SO2_CAL_HI_BYTE:   DS   1
             ;
             ;  Temporary floating point values.
             ;
                      PUBLIC   CNVTMP
00BC         CNVTMP:  DS       4                ; Floating point temp for conversion routines
             ;
                      PUBLIC   FNCTM1,FNCTM2,FNCTM3,XSRTMP
                                                ; Temporaries for intermediate function values
00C0         FNCTM1:  DS       4
00C4         FNCTM2:  DS       4
00C8         FNCTM3:  DS       4
             ;
```

```
003C              FSRTMP  EQU     CNVTMP          ; Temporary for polynomial evaluation
                  ;=============== End of FPAC/DPAC variable declarations ===============
                  ;
007F              FBIAS   EQU     127
                  ;
0001              ERUNF   EQU     1               ;FPERR UNDERFLOW ERROR CODE
0002              EROVF   EQU     2               ;FPERR OVERFLOW ERROR CODE
0003              ENNAN   EQU     3               ;FPERR INVALID OPERATION ERROR CODE

                  ;BEGIN PROGRAM;
                  MYCSEG  SEGMENT CODE
----                      RSEG    MYCSEG          ; External ROM
0000 758120                       MOV SP,#0FH     ;make SP point to 0FH (end of RB2)
0003 020000                       JMP INIT        ;GO!
003F C1
0040 A7
0041 39
0042 0C                   DB      00CH,094H,016H,0BCH     ; -9.1982E-3
0043 94
0044 16
0045 BC
0046 CD                   DB      0CDH,05CH,0C0H,03DH     ;  9.3927E-2
0047 5C
0048 C0
0049 3D
004A 09                   DB      009H,08AH,057H,040H     ;  3.3678
004B 8A
004C 57
004D 40
  0004            F2N     EQU     4

004E EF           SO2COR: DB      0EFH,03DH,0FEH,037H     ; 3.0308E-5
004F 3D
0050 FE
0051 37
0052 17                   DB      017H,008H,0C8H,039H     ; 3.8153E-4
0053 08
0054 C8
0055 39
0056 18                   DB      018H,021H,02CH,03FH     ; 0.67238
0057 21
0058 2C
0059 3F
005A 39                   DB      039H,062H,025H,03FH     ; 0.64603
005B 62
005C 25
005D 3F
  0004            SO2N    EQU     4

                  ; misc constants
005E 00           BIN_ROM_H3_CAL_OFFSET:  DB      000H,000H,000H,03FH     ;  0.5
005F 00
0060 00
0061 3F
0062 00           BIN_ROM_SO2_CAL_OFFSET: DB      000H,000H,000H,0BFH     ; -0.5
0063 00
0064 00
0065 BF
0066 00           FP0:    DB      000H,000H,000H,000H     ;  0
0067 00
0068 00
0069 00
006A 00           BIN_ROM_H3_CAL_SCALE:   DB      000H,000H,075H,045H     ;  3920.0
006B 00
006C 75
```

```
006D 45
006E [illegible]
006F [illegible]      317    BIN_ROM_SO2_CAL_SCALE:  DB      000H,080H,06DH,045H      ;  3800.0

LOC  OBJ             LINE   SOURCE

                     271    ;
                     272    ;TIMER0 INTERRUPT ROUTINE:
                     273    ;
000B                 274                     ORG 000BH
000B C28C            275                     CLR TCON.4          ;turn off TIMER0
000D 32              276                     RETI                ;return to pausing looper,
                     277
                     278    ;MESSAGES
000E 5653454E        279    VSENSE:    DB   'VSENSE= '          ;8
0012 53453D20
0016 4348[illegible]45   280    ERRMSG:    DB   'CH ERROR'          ;8 characters
001A 5252[illegible]
                     281    ;
                     282    ;fpac51 stuff begin
                     283    ;
                     284    ; F1, IR oxy
001E 31              285    F1COF:   DB      031H,08CH,0F6H,081H      ;  -7.17548E-9
001F 8C
0020 F6
0021 81
0022 27              286             DB      027H,0CEH,042H,038H      ;   4.64452E-5
0023 CE
0024 42
0025 38
0026 2D              287             DB      02DH,0E9H,0E8H,0BDH      ;  -1.13726E-1
0027 E9
0028 E8
0029 BD
002A 96              288             DB      096H,0D2H,000H,043H      ; 128.8226
002B D2
002C 00
002D 43
  0004               289    F1N      EQU     4
                     290
                     291    ;F3, IR/R   oxy
002E 1A              292    F3COF:   DB      01AH,053H,08FH,0B9H      ; -2.7337E-4
002F 53
0030 8F
0031 B9
0032 F2              293             DB      0F2H,098H,081H,03CH      ;  1.5820E-2
0033 98
0034 81
0035 3C
0036 21              294             DB      021H,0EAH,09EH,0BEH      ; -0.31038
0037 EA
0038 9E
0039 BE
003A 15              295             DB      015H,01DH,019H,040H      ;  2.3924
003B 1D
003C 19
003D 40
  0004               296    F3N      EQU     4
                     297
                     298    ;F2, IR/R DE
003E A5              299    F2COF:   DB      0A5H,[illegible]H,0A7H,039H      ;  3.1997E-4
```

```
LOC  OBJ              LINE     SOURCE

0070 6D
0071 45
                       318
0072 00                319     FP1:     DB       000H,000H,080H,03FH      ;  1.0
0073 00
0074 80
0075 3F
0076 00                320     FP2:     DB       000H,000H,000H,040H      ;  2.0
0077 00
0078 00
0079 40
007A 00                321     FP5:     DB       000H,000H,0A0H,040H      ;  5.0
007B 00
007C A0
007D 40
007E 00                322     FP95:    DB       000H,000H,0BEH,042H      ; 95.0
007F 00
0080 BE
0081 42
                       323
0082 52                324     HBHCT:   DB       052H,088H,09EH,03EH      ; 0.3100
0083 88
0084 9E
0085 3E
                       325     ;
                       326     ;fpac51 stuff end
                       327
                       328     ;start by setting up interrupts, TIMER0 control, and then
                       329     ;clear LCD display by writing the command sequence:
                       330     ;    38H, 38H, 01H, 0FH, 06H, 80H, 0EH
                       331     ;
0086 753931            332     INIT:             MOV TMOD,#031H       ;set up TMOD register to disable
                       333                                            ; TIMER1 and to set up TIMER0 to
                       334                                            ; run as a 16-bit timer when enabled
                       335                                            ; by TCON.4=1
0089 C28C              336                       CLR TCON.4           ;make sure TIMER0 is off until needed
008B 75A882            337                       MOV IE,#082H         ;set up the interrupt register to
                       338                                            ; recognize a TIMER0 interrupt
008E 74FF              339                       MOV A,#0FFH          ;set up A w/ all 1's in order to
0090 F590              340                       MOV P1,A             ; explicitly clear Port 1 so that
                       341                                            ; VREF & VCCS are off, and
                       342                                            ; a grounded MUX channel is selected
0092 120000    F       343                       LCALL CDLY           ;delay while display resets
0095 120000    F       344                       LCALL CDLY           ; from power-on condition
0098 900000            345                       MOV DPTR,#DSPCOM     ;set up DPTR w/ DISPLAY address
009B 7438              346                       MOV A,#038H          ;set up A w/ DISPLAY initialize cmd
009D F0                347                       MOVX @DPTR,A         ;write it out to the display
009E 120000    F       348                       LCALL CDLY           ;delay for appropriate command time
00A1 F0                349                       MOVX @DPTR,A         ;repeat
00A2 120000    F       350                       LCALL CDLY
00A5 120000    F       351                       LCALL CLRDSP         ;clear the display
00A8 740F              352                       MOV A,#0FH           ;set up A w/ DISPLAY ON
00AA F0                353                       MOVX @DPTR,A         ;
00AB 120000    F       354                       LCALL CDLY           ;
00AE 7406              355                       MOV A,#06H           ;set up A w/ DISPLAY entry mode
LOC  OBJ              LINE     SOURCE

00B0 F0                356                       MOVX @DPTR,A         ;
00B1 120000    F       357                       LCALL CDLY           ;
00B4 740E              358                       MOV A,#0EH           ;set up A w/ DISPLAY hold
00B6 F0                359                       MOVX @DPTR,A         ;
00B7 120000    F       360                       LCALL CDLY           ;
```

```
                        ;
                        ;now initialize the 8255
                        ;
008A 90A003                             MOV DPTR,#CSR       ;set up DPTR w/ add of 8255 CSR
008D 749B                               MOV A,#09BH         ;set up A w/ mode control word to
                                                            ;make all ports inputs
008F F0                                 MOVX @DPTR,A        ;

                        ;now initialize the D/A for current source
00C0 7400                               MOV A,#00H          ;set up A/D for ? 0 volts
00C2 120000       F                     LCALL LOADA         ;update the D/A w/ the offset
00C5 120000       F                     LCALL CDLY          ;let VCCS settle

                        ;
                        ;  MAIN PROGPAM
                        ;
00C8 120000       F     BEGIN:          LCALL CLRDSP        ;start by clearing the display
                                                            ; and setting up the MUX with
                                                            ; the desired channel for
                                                            ; conversion
                        ;
                        ;11AUG87/1043:  Add read of front panel switch to obtain channel selection.
                        ;
00CB 90A002                             MOV DPTR,#PORTC     ;point to Port C and input switch data
00CE E0                                 MOVX A,@DPTR
00CF F4                                 CPL A               ;complement A to obtain 1 corresponding
                                                            ; to channel selected
00D0 FD                                 MOV R5,A            ;store ACC in BOR5

00D1 ED                 CHS:            MOV A,R5
00D2 20E503                             JB ACC.5,CH560
00D5 020000       F                     JMP    CH4

00D8 D292               CH560:          SETB P1.2
00DA C291                               CLR  P1.1
00DC D290                               SETB P1.0

00DE C293                               CLR P1.3            ;turn on VREF
00E0 120000       F                     LCALL CDLY          ;allow VREF to settle
00E3 120000       F                     LCALL TAKE16        ;obtain an average reading
00E6 D293                               SETB P1.3           ;disable VREF

                        ;STORE RAW A/D VALUE (16 BIT SIGNED 2'S COMP)
00E8 E8                         MOV     A,R0                ;store LSB
00E9 900000       F             MOV     DPTR,#HB_CAL_LO_BYTE
00EC F0                         MOVX    @DPTR,A

00ED E9                         MOV     A,R1                ;store MSB
00EE 540F                       ANL     A,#0FH              ;zero upper nibble
00F0 900000       F             MOV     DPTR,#HB_CAL_HI_BYTE
LOC  OBJ           LINE    SOURCE

00F3 F0                         MOVX    @DPTR,A

00F4 120000       F             LCALL   HEXOUT

00F7 D292                               SETB P1.2
00F9 D291                               SETB P1.1
00FB D290                               SETB P1.0

00FD C293                               CLR P1.3            ;turn on VREF
00FF 120000       F                     LCALL CDLY          ;allow VREF to settle
0102 120000       F                     LCALL TAKE16        ;obtain an average reading
0105 D293                               SETB P1.3           ;disable VREF

0107 900000                             MOV DPTR,#DSPCOM    ;point to display command register
010A 740E                               MOV A,#0EOH         ;set up A w/ 2-line command
010C F0                                 MOVX @DPTR,A        ;and actually set LM2020 into 2-line mode
010D 120000       F                     LCALL CDLY          ;
```

```
                      ;STORE RAW VALUE
0110 E8                      MOV    A,R0                    ;store LSD
0111 900000        F         MOV    DPTR,#S02_CAL_LO_BYTE
0114 F0                      MOVX   @DPTR,A

0115 E9                      MOV    A,R1                    ;store MSB
0116 540F                    ANL    A,#0FH                  ;zero upper nibble
0118 900000        F         MOV    DPTR,#S02_CAL_HI_BYTE
011B F0                      MOVX   @DPTR,A

011C 120000        F         LCALL  WEXOUT
011F 120000        F         LCALL  ONE
0122 120000        F         LCALL  CLRDSP

0125 80A1                    JMP    BEGIN

                      CH4:   MOV    A,R5                    ;if ACC.4 isn't 1, then go handle as
0127 ED                      JNB    ACC.4,CH3               ; CH#3, else, it's CH#4, so do what's
0128 30E4A8                  SETB   P1.2                    ; needed for VSENSE...
012B D292                    CLR    P1.1                    ; first, set up MUX address of 100
012D C291                    CLR    P1.0
012F C290                    MOV    DPTR,#VSENSE            ;BACKHERE, write out "VSENSE ="
0131 900000        F         MOV    R6,#00H
0134 7E00                    LCALL  WRITE
0136 120000        F
                             LCALL  TAKE16                  ;obtain an average reading
0139 120000        F
                             LCALL  SCALE                   ;scale it by 1.221 mV/step
013C 120000        F         LCALL  BCDHI                   ;convert the binary number to BCD
013F 120000        F         LCALL  WRITEV                  ;write out the voltage
0142 120000        F         LCALL  ONE                     ;
0145 120000        F         LCALL  CLRDSP                  ;
0148 120000        F
                             MOV    DPTR,#VSENSE            ;turn LED on and do it again
014B 900000        F         MOV    R6,#00H                 ;write out "VSENSE ="
014E 7E00                    LCALL  WRITE                   ;
0150 120000        F
LOC  OBJ               LINE  SOURCE

0153 C293                    CLR    P1.3                    ;turn on VREF
0155 C294                    CLR    P1.4                    ;turn on VCCS
0157 120000        F         LCALL  CDLY                    ;allow VREF to settle
015A 120000        F         LCALL  TAKE16                  ;obtain an average reading
015D D293                    SETB   P1.3                    ;disable VREF
015F D294                    SETB   P1.4                    ;disable VCCS

0161 120000        F         LCALL  SCALE                   ;scale it by 1.221 mV/step
0164 120000        F         LCALL  BCDHI                   ;convert the binary number to BCD
0167 120000        F         LCALL  WRITEV                  ;write out the voltage
016A 120000        F         LCALL  ONE                     ;
016D 120000        F         LCALL  CLRDSP                  ;
0170 020000        F         JMP    BEGIN                   ;

0173 ED               CH3:   MOV    A,R5                    ;if ACC.3 isn't 1, then go handle as
0174 30E313                  JNB    ACC.3,CH2               ; CH#2, else, it's CH#3, so do what's
0177 C292                    CLR    P1.2                    ; needed for 50xVDET...
0179 D291                    SETB   P1.1                    ; start by setting MUX address 111
017B C290                    CLR    P1.0

017D 7433                    MOV    A,#33H                  ;write a 3 and a blank
017F 120000        F         LCALL  WRITEB
0182 7420                    MOV    A,#20H
0184 120000        F         LCALL  WRITEB

0187 020000        F         JMP    FISHIN                  ;go fishin'

018A ED               CH2:   MOV    A,R5                    ;if ACC.3 isn't 1, then go handle as
018B 20E203                  JB     ACC.2,CH260             ; CH#1, else, it's CH#2, so do what's
018E 020000        F         JMP    CH0

                      CH260:
                                                            ; needed for 20xVDET...
0191 C292                    CLR    P1.2                    ; establish MUX address of 001
0193 C291                    CLR    P1.1
```

```
0195 D290              501                  SETB P1.0              ;
                       502
0197 7432              503                  MOV A,#32H             ;write a 2 and a blank
0199 120000      F     504                  LCALL WRITEB
019C 7420              505                  MOV A,#20H
019E 120000      F     506                  LCALL WRITEB
                       507
01A1 020000      F     508                  JMP FISHIN             ;go fishin'
                       509
01A4 ED                510      CH1:        MOV A,R5               ;restore channel mask
01A5 30E100            511                  JNB ACC.1,CH1GO          ;if ACC.1 isn't 1, then it's CH#0,
01A8 020000      F     512                  JMP CH0
                       513
01AB D292              514      CH1GO:      SETB P1.2              ; else it's CH#1, so do what's
01AD C291              515                  CLR  P1.1              ; needed for 10xVDET
01AF D290              516                  SETB P1.0              ;establish MUX address of 001
                       517                                         ;fall thru... go fishin'
                       518
01B1 7431              519                  MOV A,#31H             ;write a 1 and a blank
01B3 120000      F     520                  LCALL WRITEB
LOC  OBJ               LINE     SOURCE

0211 20E00E            576            JB ACC.0,CHOGO
                       577
0214 900000      F     578            MOV DPTR,#ERRMSG
0217 7E03              579            MOV R6,#03H
0219 120000      F     580            LCALL WRITE
021C 120000      F     581            LCALL ONE
021F 020000      F     582            JMP BEGIN
                       583
0222 D292              584      CHOGO:      SETB P1.2
0224 C291              585                  CLR  P1.1
0226 D290              586                  SETB P1.0
                       587
0228 C293              588                  CLR P1.3               ;turn on VREF
022A 120000      F     589                  LCALL CDLY             ;allow VREF to settle
022D 120000      F     590                  LCALL TAKE16           ;obtain an average reading
                       591
                       592      ;STORE RAW A/D VALUE (16 BIT SIGNED 2'S COMP)
0230 E8                593            MOV     A,R0             ;store LSB
0231 900000      F     594            MOV     DPTR,#HB_CAL_LO_BYTE
0234 F0                595            MOVX    @DPTR,A
                       596
0235 E9                597            MOV     A,R1             ;store MSB
0236 540F              598            ANL     A,#0FH           ;zero upper nibble
0238 900000      F     599            MOV     DPTR,#HB_CAL_HI_BYTE
023B F0                600            MOVX    @DPTR,A
                       601
                       602      ;FLOAT RAW VALUE TO OBTAIN BINARY FLOATING POINT
023C 900000      F     603            MOV     DPTR,#HB_CAL_HI_BYTE            ;put MSB in B
023F E0                604            MOVX    A,@DPTR
0240 F5F0              605            MOV     B,A
0242 900000      F     606            MOV     DPTR,#HB_CAL_LO_BYTE            ;put LSB in A
0245 E0                607            MOVX    A,@DPTR
0246 120000      F     608            CALL    FLOAT                     ; convert integer to FP
                       609
                       610      ;Divide by BIN_ROM_HB_CAL_SCALE
0249 900000      F     611            MOV     DPTR,#BIN_ROM_HB_CAL_SCALE
024C D200        F     612            SETB    FACRNM
024E 120000      F     613            CALL    FPDIV
                       614      ;Add 0.5
0251 900000      F     615            MOV     DPTR,#BIN_ROM_HB_CAL_OFFSET
0254 D200        F     616            SETB    FACRNM
0256 120000      F     617            CALL    FPADD
                       618
```

```
                        619    ;STORE RESULT, IR refl constant for HB calibration
0259 900000     F       620            MOV     DPTR,#BIN_RAM_HB_CAL        ; destination
025C 120000     F       621            CALL    STFAC               ; store FAC
                        622
025F 900000     F       623            MOV     DPTR,#ASC_RAM_HB_CAL
0262 120000     F       624            CALL    BINASC
                        625
0265 D292               626                    SETB P1.2
0267 D291               627                    SETB P1.1
0269 D290               628                    SETB P1.0
                        629
026B 120000     F       630                    LCALL TAKE16        ;obtain an average reading
LOC  OBJ                LINE   SOURCE
01B4 7420                                      MOV A,#20H
01B6 120000     F                              LCALL WRITEB
                               FISHIN:
                               ;first current  source
01B9 C293                                      CLR P1.3            ;turn on VREF
01BB C294                                      CLR P1.4            ;turn on VCCS
01BD 120000     F                              LCALL CDLY          ;allow VREF to settle
01C0 120000     F                              LCALL TAKE16        ;average 16 values
01C3 D293                                      SETB P1.3           ;disable VREF
01C5 D294                                      SETB P1.4           ;disable VCCS
01C7 120000     F                              LCALL HEXOUT        ;
01CA 120000     F                              LCALL ONE           ;delay a second here...
01CD E8                                MOV     A,R0                ;store LSB
01CE 900000     F                      MOV     DPTR,#INFRARED_LO_BYTE
01D1 F0                                MOVX    @DPTR,A
01D2 E9                                MOV     A,R1                ;store MSB
01D3 540F                              ANL     A,#0FH              ;zero upper nibble
01D5 900000     F                      MOV     DPTR,#INFRARED_HI_BYTE
01D8 F0                                MOVX    @DPTR,A
                               ;second current source
01D9 C293                                      CLR P1.3            ;turn on VREF
01DB C295                                      CLR P1.5            ;turn on VCCS
01DD 120000     F                              LCALL CDLY          ;allow VREF to settle
01E0 120000     F                              LCALL TAKE16        ;average 16 values
01E3 D293                                      SETB P1.3           ;disable VREF
01E5 D295                                      SETB P1.5           ;disable VCCS
01E7 900000                                    MOV DPTR,#DSPCOM    ;point to display command register
01EA 74C0                                      MOV A,#0C0H         ;set up A w/ 2-line command
01EC F0                                        MOVX @DPTR,A        ;and actually set LM2020 into 2-line mode
01ED 120000     F                              LCALL CDLY          ;
01F0 120000     F                              LCALL HEXOUT        ;
01F3 120000     F                              LCALL ONE           ;delay a second here...
01F6 120000     F                              LCALL ONE           ;delay a second here...
01F9 120000     F                              LCALL ONE           ;delay a second here...
01FC E8                                MOV     A,R0                ;store LSB
01FD 900000     F                      MOV     DPTR,#RED_LO_BYTE
0200 F0                                MOVX    @DPTR,A
0201 E9                                MOV     A,R1                ;store MSB
0202 540F                              ANL     A,#0FH              ;zero upper nibble
0204 900000     F                      MOV     DPTR,#RED_HI_BYTE
0207 F0                                MOVX    @DPTR,A
0208 120000     F                              LCALL CLRDSP        ;
020B 020000     F                              JMP BEGIN
020E ED                        CHO:    MOV A,R5
LOC  OBJ                LINE   SOURCE
026E D293               631                    SETB P1.3           ;disable VREF
0270 120000     F       632                    LCALL CDLY
                        633
                        634    ;STORE RAW VALUE
0273 E8                 635            MOV     A,R0                ;store LSB
0274 900000     F       636            MOV     DPTR,#SO2_CAL_LO_BYTE
0277 F0                 637            MOVX    @DPTR,A
```

```
0278 E9                      MOV     A,R1                            ;store MSB
0279 540F                    ANL     A,#0FH                          ;zero upper nibble
027B 900000      F           MOV     DPTR,#SO2_CAL_HI_BYTE
027E F0                      MOVX    @DPTR,A

                        ;FLOAT RAW VALUE
027F 900000      F           MOV     DPTR,#SO2_CAL_HI_BYTE                       ;put MSB in B
0282 E0                      MOVX    A,@DPTR
0283 F5F0                    MOV     B,A
0285 900000      F           MOV     DPTR,#SO2_CAL_LO_BYTE                       ;put LSB in A
0288 E0                      MOVX    A,@DPTR
0289 120000      F           CALL    FLOAT                             ; convert integer to FP

                        ;Divide by @IN_ROM_SO2_CAL_SCALE
028C 900000      F           MOV     DPTR,#BIN_ROM_SO2_CAL_SCALE
028F D200        F           SETB    FACPNM
0291 120000      F           CALL    FPDIV
                        ;Add -0.5
0294 900000      F           MOV     DPTR,#BIN_ROM_SO2_CAL_OFFSET
0297 D200        F           SETB    FACRNM
0299 120000      F           CALL    FPADD

                        ;STORE BINARY VALUE, Log ratio offset for PO2 Calibration
029C 900000      F           MOV     DPTR,#BIN_RAM_SO2_CAL                 ; destination
029F 120000      F           CALL    STFAC                             ; store FAC

02A2 900000      F           MOV     DPTR,#ASC_RAM_SO2_CAL
02A5 120000      F           CALL    BINASC

02A8 7430                    MOV A,#30H                       ; WRITE A ZERO AND A BLANK
02AA 120000      F           LCALL WRITEB
02AD 7420                    MOV A,#20H
02AF 120000      F           LCALL WRITEB

02B2 C292                    CLR    P1.2                      ; X50 FOR 800 LED
02B4 D291                    SETB   P1.1
02B6 C290                    CLR    P1.0

02B8 C293                    CLR    P1.3                      ; TAKE 16 SAMPLES AND AVERAGE THEM
02BA C294                    CLR    P1.4
02BC 120000      F           LCALL CDLY
02BF [illegible] F           LCALL TAKE16
02C2 D293                    SETB P1.3
02C4 D294                    SETB P1.4

02C6 120000      F           LCALL HEXOUT                     ; DISPLAY RAW DATA IN HEX
02C9 120000      F           LCALL ONE
LOC  OBJ                LINE     SOURCE

02CC E8                      MOV A,R0                         ; STORE LSB
02CD 900000      F           MOV DPTR,#INFRARED_LO_BYTE
02D0 F0                      MOVX @DPTR,A

02D1 E9                      MOV A,R1                         ; STORE MSB
02D2 540F                    ANL A,#0FH                       ; ZERO UPPER NIBBLE
02D4 900000      F           MOV DPTR,#INFRARED_HI_BYTE
02D7 F0                      MOVX @DPTR,A

02D8 C292                    CLR    P1.2                      ; X20 FOR 660 LED
02DA C291                    CLR    P1.1
02DC D290                    SETB   P1.0
```

```
02DE C293                     CLR    P1.3              ; TAKE 16 SAMPLES AND AVERAGE THEM
02E0 C295                     CLR    P1.5
02E2 120000      F            LCALL  CDLY
02E5 120000      F            LCALL  TAKE16
02E8 D293                     SETB   P1.3
02EA D295                     SETB   P1.5

02EC 900000                   MOV DPTR,#DSPCOM         ; PUT DISPLAY IN TWO LINE MODE
02EF 74C0                     MOV A,#0C0H
02F1 F0                       MOVX @DPTR,A
02F2 120000      F            LCALL CDLY

02F5 120000      F            LCALL HEXOUT             ; DISPLAY RAW DATA IN HEX
02F8 120000      F            LCALL ONE
02FB 120000      F            LCALL ONE
02FE 120000      F            LCALL ONE

0301 E3                       MOV A,P0
0302 900000      F            MOV DPTR,#RED_LO_BYTE
0305 F0                       MOVX @DPTR,A

0306 E9                       MOV A,P1
0307 540F                     ANL A,#0FH
0309 900000      F            MOV DPTR,#RED_HI_BYTE
030C F0                       MOVX @DPTR,A

030D 120000      F            LCALL CLRDSP

                        ;fpac51 stuff begin
                        ;
                        ; ***************************************************************
                        ;
                        ; convert raw InfraRed Reflectance integer to floating point value x1
0310 900000      F             MOV     DPTR,#INFRARED_HI_BYTE        ;put MSB in B
0313 E0                        MOVX    A,@DPTR
0314 F5F0                      MOV     B,A
0316 900000      F             MOV     DPTR,#INFRARED_LO_BYTE        ;put LSB in A
0319 E0                        MOVX    A,@DPTR
031A 120000      F             CALL    FLOAT                  ; convert integer to FP
                        ;       MOV     DPTR,#FP2              ; point to value
                        ;       SETB    FACPNM                 ; in ROM

LOC  OBJ               LINE    SOURCE
                        ;       CALL    FPMUL                  ; multiply by FAC
                        ;multiply by IR refl constant for MB calibration
031D 900000      F             MOV     DPTR,#MIN_RAW_MB_CAL
0320 120000      F             CALL    FPMUL

                        ; store InfraRed floating point value
0323 900000      F             MOV     DPTR,#MIN_RAW_INFRARED_DATA    ; destination
0326 120000      F             CALL    STFAC                  ; store FAC

0329 900000      F             MOV     DPTR,#ABC_RAW_INFRARED_DATA
032C 120000      F             CALL    MINASC

                        ; convert raw Red Reflectance integer to floating point value x1
032F 900000      F             MOV     DPTR,#RED_HI_BYTE      ;put MSB in B
0332 E0                        MOVX    A,@DPTR
0333 F5F0                      MOV     B,A
0335 900000      F             MOV     DPTR,#RED_LO_BYTE      ;put LSB in A
0338 E0                        MOVX    A,@DPTR
0339 120000      F             CALL    FLOAT                  ; convert integer to FP
                        ;       MOV     DPTR,#FP2              ; point to value
                        ;       SETB    FACPNM                 ; in ROM
                        ;       CALL    FPMUL                  ; multiply by FAC

                        ; store Red floating point value
033C 900000      F             MOV     DPTR,#MIN_RAW_RED_DATA ; destination
033F 120000      F             CALL    STFAC                  ; store FAC
```

```
0343 900003  F          MOV     DPTR,#ASC_RAM_RED_DATA
0345 120003  F          CALL    BINASC
                  ; ********************************************************
                  ;
                  ; obtain IR/R ratio
0348 900000  F          MOV     DPTR,#BIN_RAM_INFRARED_DATA         ; point to IR value
034B 120003  F          CALL    LDFAC                 ; load IR into FAC
034E 900000  F          MOV     DPTR,#BIN_RAM_RED_DATA          ; point to Red value
0351 120003  F          CALL    FPDIV             ; divide Red into IR
                  ;       CALL    FPLOG             ; get log of ratio
                  ;
                  ; store log ratio
0354 900000  F          MOV     DPTR,#BIN_RAM_LOG_RATIO                 ; destination
0357 120000  F          CALL    STFAC             ; store FAC
                  ;
                  ; convert log ratio (binary floating point) to ASCII
035A 900000  F          MOV     DPTR,#ASC_RAM_LOG_RATIO
035D 120000  F          CALL    BINASC            ; convert binary to ASCII
                  ;
                  ; ********************************************************
                  ;
                  ; evaluate F1 polynomial (HCT), SCALE IT TO HB and save it
0360 900000  F          MOV     DPTR,#BIN_RAM_INFRARED_DATA        ; point to F1 result
0363 120000  F          CALL    LDFAC             ; load into FAC
0366 900000  F          MOV     DPTR,#F1COF       ; point to first coefficient
LOC  OBJ          SOURCE

0369 7404               MOV     A,#F1N                         ; get number of coeff's
036B 120000  F          CALL    XSER                           ; evaluate polynomial using FAC
036E 900000  F          MOV     DPTR,#HBHCT                  ; POINT TO SCALE FACTOR
0371 D200               SETB    FACRNM                         ; IN ROM
0373 120000  F          CALL    FPMUL                          ; MUL BY FAC
0376 900000  F          MOV     DPTR,#BIN_RAM_HB                  ; destination
0379 120000  F          CALL    STFAC                          ; store FAC
                  ;
                  ; convert F1 binary (floating point) result to ASCII
037C 900000  F          MOV     DPTR,#ASC_RAM_HB
037F 120000  F          CALL    BINASC                         ; convert binary to ASCII
                  ;
                  ; ***************************************************************
                  ;
                  ; evaluate F2 polynomial (Deoxy end-point)
0382 900000  F          MOV     DPTR,#BIN_RAM_HB                  ; point to F1 result
0385 120000  F          CALL    LDFAC                          ; load into FAC
0388 900000  F          MOV     DPTR,#F2COF                    ; point to first coefficient
038B 7404               MOV     A,#F2N                         ; get number of coeff's
038D 120000  F          CALL    XSER                           ; evaluate polynomial using FAC
                  ;       CALL    FPLOG                          ; take log of FAC
                  ;
                  ; store F2 result
0390 900000  F          MOV     DPTR,#BIN_RAM_DEOXY_END_POINT              ; destination
0393 120000  F          CALL    STFAC                          ; store FAC
                  ;
                  ; convert F2 result (binary floating point) to ASCII
0396 900000  F          MOV     DPTR,#ASC_RAM_DEOXY_END_POINT
0399 120000  F          CALL    BINASC                         ; convert binary to ASCII
                  ;
                  ; evaluate F3 polynomial (Oxy end-point)
039C 900000  F          MOV     DPTR,#BIN_RAM_HB                  ; point to F1 result
039F 120000  F          CALL    LDFAC                          ; load into FAC
03A2 900000  F          MOV     DPTR,#F3COF                    ; point to first coefficient
03A5 7404               MOV     A,#F3N                         ; get number of coeff's
03A7 120000  F          CALL    XSER                           ; evaluate polynomial using FAC
                  ;       CALL    FPLOG                          ; take log of FAC
                  ;
                  ; store F3 result
03AA 900000  F          MOV     DPTR,#BIN_RAM_OXY_END_POINT               ; destination
03AD 120000  F          CALL    STFAC                          ; store FAC
                  ;
                  ; convert F3 result (binary floating point) to ASCII
```

```
0383 900000   F          MOV     DPTR,#ASC_RAM_OXY_END_POINT
0383 120000   F          CALL    BINASC                  ; convert binary to ASCII
                   ;
                   ; ***********************************************************
                   ;
                   ; subtract Deoxy end-point from Oxy end-point and save it
0386 900000   F          MOV     DPTR,#MIN_RAM_DEOXY_END_POINT       ; point to Oxy
0389 120000   F          CALL    LDFAC                   ; load into FAC
03BC B200     F          CPL     FACSGN                  ; flip the sign
03BE 900000   F          MOV     DPTR,#MIN_RAM_OXY_END_POINT         ; point to Deoxy
03C1 120000   F          CALL    FPADD                   ; add to FAC
LOC  OBJ           LINE     SOURCE
03C4 900000   F          MOV     DPTR,#MIN_RAM_SO2       ; destination
03C7 120000   F          CALL    STFAC                   ; store FAC
                   ; subtract Deoxy end-point from log ratio
03CA 900000   F          MOV     DPTR,#MIN_RAM_DEOXY_END_POINT       ; point to Oxy
03CD 120000   F          CALL    LDFAC                   ; load into FAC
03D0 B200     F          CPL     FACSGN                  ; flip the sign
03D2 900000   F          MOV     DPTR,#MIN_RAM_LOG_RATIO ; point to log ratio
03D5 120000   F          CALL    FPADD                   ; add to FAC
                   ; ADD LOG RATIO OFFSET FOR OX CAL
03D8 900000   F          MOV     DPTR,#MIN_RAM_SO2_CAL
03DB 120000   F          CALL    FPADD
                   ; divide first difference into second difference
03DE 900000   F          MOV     DPTR,#MIN_RAM_SO2       ; point first diff
03E1 120000   F          CALL    FPDIV                   ; divide into FAC
                   ; finish interpolation
03E4 900000   F          MOV     DPTR,#FP95              ; point to 95.0
03E7 D200     F          SETB    FACRNM                  ; it's in code seg
03E9 120000   F          CALL    FPMUL                   ; multiply by FAC
03EC 900000   F          MOV     DPTR,#FP5               ; point to 5.0
03EF D200     F          SETB    FACRNM                  ; it's in code seg
03F1 120000   F          CALL    FPADD                   ; add to FAC

03F4 900000   F          MOV     DPTR,#SO2COR
03F7 7400     F          MOV     A,#SO2N
03F9 120000   F          CALL    RSER
                   ; convert floating point result (binary) to ASCII
03FC 900000   F          MOV     DPTR,#ASC_RAM_SO2
03FF 120000   F          CALL    BINASC                  ; convert binary to ASCII
                   ;fpac51 stuff end
0402 900000   F               MOV DPTR,#ASC_RAM_HB
0405 120000   F               LCALL WRITP
                   ;              LCALL ONE          ;delay a second here...
                   ;              LCALL ONE          ;delay a second here...
                   ;              LCALL ONE          ;delay a second here...
0408 900000                    MOV DPTR,#DSPCOM    ;point to display command register
040B 7400                      MOV A,#COM          ;set up A w/ 2-line command
040D F0                        MOVX @DPTR,A        ;and actually set LM2020 into 2-line mode
040E 120000   F               LCALL COLY
                   ;              LCALL CLRDSP       ;
0411 900000   F               MOV DPTR,#ASC_RAM_SO2
0414 120000   F               LCALL WRITP         ;
0417 120000   F               LCALL ONE           ;delay a second here...
041A 120000   F               LCALL ONE           ;delay a second here...

N A M E                 T Y P E   V A L U E     A T T R I B U T E S

FPLOG . . . . . . . . . C ADDR    ----          EXT
FPMUL . . . . . . . . . C ADDR    ----          EXT
FPRDIV. . . . . . . . . C ADDR    ----          EXT
FPSIN . . . . . . . . . C ADDR    ----          EXT
FPSQRT. . . . . . . . . C ADDR    ----          EXT
FPTAN . . . . . . . . . C ADDR    ----          EXT
```

```
FPXTOI. . . . . . . . . .  C ADDR   ----          EXT
HR_CAL_HI_BYTE. . . . . .  X ADDR   0099H    R          SEG=XDRSEG
HR_CAL_LO_BYTE. . . . . .  X ADDR   0098H    R          SEG=XDRSEG
HURCT . . . . . . . . . .  C ADDR   0082H    R          SEG=MYCSEG
HEXOUT. . . . . . . . . .  C ADDR   ----          EXT
IE. . . . . . . . . . . .  D ADDR   00A8H    A
INFRARED_HI_BYTE. . . . .  X ADDR   0085H    R          SEG=XDRSEG
INFRARED_LO_BYTE. . . . .  X ADDR   0084H    R          SEG=XDRSEG
INIT. . . . . . . . . . .  C ADDR   0086H    R          SEG=MYCSEG
INT . . . . . . . . . . .  C ADDR   ----          EXT
LDFAC . . . . . . . . . .  C ADDR   ----          EXT
LOADA . . . . . . . . . .  C ADDR   ----          EXT
MANSGN. . . . . . . . . .  B ADDR   0001H.5  R    PUB   SEG=DBRSEG
MYCSEG. . . . . . . . . .  C SEG    0432H               REL=UNIT
NANFLG. . . . . . . . . .  B ADDR   0000H.4  R    PUB   SEG=DBRSEG
ONE . . . . . . . . . . .  C ADDR   ----          EXT
OVFFLG. . . . . . . . . .  B ADDR   0000H.3  R    PUB   SEG=DBRSEG
P1. . . . . . . . . . . .  D ADDR   0090H    A
PHI4. . . . . . . . . . .    ----   ----
PORTA . . . . . . . . . .  X ADDR   A000H    A    PUB
PORTB . . . . . . . . . .  X ADDR   A001H    A    PUB
PORTC . . . . . . . . . .  X ADDR   A002H    A    PUB
READAD. . . . . . . . . .  C ADDR   ----          EXT
RED_HI_BYTE . . . . . . .  X ADDR   0097H    R          SEG=XDRSEG
RED_LO_BYTE . . . . . . .  X ADDR   0096H    R          SEG=XDRSEG
SCALE . . . . . . . . . .  C ADDR   ----          EXT
SIGFLG. . . . . . . . . .  B ADDR   0001H.6  R    PUB   SEG=DBRSEG
SO2_CAL_HI_BYTE . . . . .  X ADDR   009BH    R          SEG=XDRSEG
SO2_CAL_LO_BYTE . . . . .  X ADDR   009AH    R          SEG=XDRSEG
SO2COR. . . . . . . . . .  C ADDR   034EH    R          SEG=MYCSEG
SO2N. . . . . . . . . . .    NUMB   0004H    A
SP. . . . . . . . . . . .  D ADDR   0081H    A
STFAC . . . . . . . . . .  C ADDR   ----          EXT
TOHI. . . . . . . . . . .    NUMB   00FEH    A
TOLOW . . . . . . . . . .    NUMB   00C0H    A
TAKE16. . . . . . . . . .  C ADDR   ----          EXT
TCON. . . . . . . . . . .  D ADDR   0088H    A
TMOD. . . . . . . . . . .  D ADDR   0089H    A
UNFFLG. . . . . . . . . .  B ADDR   0000H.2  R    PUB   SEG=DBRSEG
VSENSE. . . . . . . . . .  C ADDR   0000H    R          SEG=MYCSEG
WRITE . . . . . . . . . .  C ADDR   ----          EXT
WRITED. . . . . . . . . .  C ADDR   ----          EXT
WRITED. . . . . . . . . .  C ADDR   ----          EXT
WRITEV. . . . . . . . . .  C ADDR   ----          EXT
WRTFP . . . . . . . . . .  C ADDR   ----          EXT
XDRSEG. . . . . . . . . .  X SEG    00CCH               REL=UNIT
XSER. . . . . . . . . . .  C ADDR   ----          EXT
XSRTMP. . . . . . . . . .  X ADDR   00C2H    R    PUB   SEG=XDRSEG
XXSER . . . . . . . . . .  C ADDR   ----          EXT

LOC  OBJ            LINE     SOURCE

0420 120000   F      906              LCALL ONE         ;delay a second here...
                     907
0423 120000   F      908              LCALL ONE
0426 120000   F      909              LCALL ONE
0429 120000   F      910              LCALL ONE
                     911
042C 120000   F      912              LCALL CLRDSP      ;
                     913
042F 020000   F      914              JMP BEGIN         ; and then go do a "normal" termination
                     915
                     916              END
```

SYMBOL TABLE LISTING

| NAME | TYPE | VALUE | | ATTRIBUTES |
|---|---|---|---|---|
| ACC . . . . . . . . . . . | D ADDR | 00F0H | A | |
| ADD5 . . . . . . . . . . | C ADDR | ---- | | EXT |
| ADD52 . . . . . . . . . . | C ADDR | ---- | | EXT |
| ADHI. . . . . . . . . . . | X ADDR | 2001H | A | PUB |
| ADLOW . . . . . . . . . . | X ADDR | 2000H | A | PUB |
| AINT. . . . . . . . . . . | C ADDR | ---- | | EXT |
| ASC_RAM_DEOXY_END_POINT | X ADDR | 0080H | R | SEG=XDRSEG |
| ASC_RAM_HB_CAL. . . . . | X ADDR | 0040H | R | SEG=XDRSEG |
| ASC_RAM_HB. . . . . . . | X ADDR | 0020H | R | SEG=XDRSEG |
| ASC_RAM_INFRARED_DATA . | X ADDR | 0000H | R | SEG=XDRSEG |
| ASC_RAM_LOG_RATIO . . . | X ADDR | 0060H | R | SEG=XDRSEG |
| ASC_RAM_OXY_END_POINT . | X ADDR | 0070H | R | SEG=XDRSEG |
| ASC_RAM_RED_DATA. . . . | X ADDR | 0010H | R | SEG=XDRSEG |
| ASC_RAM_SO2_CAL . . . . | X ADDR | 0050H | R | SEG=XDRSEG |
| ASC_RAM_SO2 . . . . . . | X ADDR | 0030H | R | SEG=XDRSEG |
| ASCBIN. . . . . . . . . | C ADDR | ---- | | EXT |
| B . . . . . . . . . . . | D ADDR | 00F0H | A | |
| BOR0. . . . . . . . . . | D ADDR | 0000H | A | PUB |
| BOR1. . . . . . . . . . | D ADDR | 0001H | A | PUB |
| BOR2. . . . . . . . . . | D ADDR | 0002H | A | PUB |
| BOR3. . . . . . . . . . | D ADDR | 0003H | A | PUB |
| BOR4. . . . . . . . . . | D ADDR | 0004H | A | PUB |
| BOR5. . . . . . . . . . | D ADDR | 0005H | A | PUB |
| BOR6. . . . . . . . . . | D ADDR | 0006H | A | PUB |
| BOR7. . . . . . . . . . | D ADDR | 0007H | A | PUB |
| BCD . . . . . . . . . . | C ADDR | ---- | | EXT |
| BCDHI . . . . . . . . . | C ADDR | ---- | | EXT |
| BEGIN . . . . . . . . . | C ADDR | 00C8H | R | SEG=MYCSEG |
| BIN_RAM_DEOXY_END_POINT | X ADDR | 00B3H | R | SEG=XDRSEG |
| BIN_RAM_HB_CAL. . . . . | X ADDR | 00A3H | R | SEG=XDRSEG |
| BIN_RAM_HB. . . . . . . | X ADDR | 0099H | R | SEG=XDRSEG |
| BIN_RAM_INFRARED_DATA . | X ADDR | 0093H | R | SEG=XDRSEG |
| BIN_RAM_LOG_RATIO . . . | X ADDR | 00ABH | R | SEG=XDRSEG |
| BIN_RAM_OXY_END_POINT . | X ADDR | 00AFH | R | SEG=XDRSEG |
| BIN_RAM_RED_DATA. . . . | X ADDR | 0097H | R | SEG=XDRSEG |
| BIN_RAM_SO2_CAL . . . . | X ADDR | 00A7H | R | SEG=XDRSEG |
| BIN_RAM_SO2 . . . . . . | X ADDR | 009FH | R | SEG=XDRSEG |
| BIN_ROM_HB_CAL_OFFSET . | C ADDR | 005EH | R | SEG=MYCSEG |
| BIN_ROM_HB_CAL_SCALE. . | C ADDR | 006AH | R | SEG=MYCSEG |
| BIN_ROM_SO2_CAL_OFFSET. | C ADDR | 0062H | R | SEG=MYCSEG |
| BIN_ROM_SO2_CAL_SCALE . | C ADDR | 006EH | R | SEG=MYCSEG |
| BINASC. . . . . . . . . | C ADDR | ---- | | EXT |
| CDLY. . . . . . . . . . | C ADDR | ---- | | EXT |
| CH0 . . . . . . . . . . | C ADDR | 0210H | R | SEG=MYCSEG |
| CH0GO . . . . . . . . . | C ADDR | 0222H | R | SEG=MYCSEG |
| CH1 . . . . . . . . . . | C ADDR | 01A4H | R | SEG=MYCSEG |
| CH1GO . . . . . . . . . | C ADDR | 01A0H | R | SEG=MYCSEG |
| CH2 . . . . . . . . . . | C ADDR | 019AH | R | SEG=MYCSEG |
| CH2GO . . . . . . . . . | C ADDR | 0191H | R | SEG=MYCSEG |
| CH3 . . . . . . . . . . | C ADDR | 0173H | R | SEG=MYCSEG |
| CHS . . . . . . . . . . | C ADDR | 00D1H | R | SEG=MYCSEG |
| CHSGO . . . . . . . . . | C ADDR | 00D8H | R | SEG=MYCSEG |
| CLRDSP. . . . . . . . . | C ADDR | ---- | | EXT |
| CNVAIT. . . . . . . . . | D ADDR | 0001H | R | SEG=DBRSEG |
| CNVTMP. . . . . . . . . | X ADDR | 000CH | R | PUB SEG=XDRSEG |
| CSR . . . . . . . . . . | X ADDR | A003H | A | PUB |
| DA1 . . . . . . . . . . | X ADDR | 4001H | A | PUB |
| DA2 . . . . . . . . . . | X ADDR | 6000H | A | PUB |
| DBRSEG. . . . . . . . . | D SEG | 0002H | | REL=BITADDRESSABLE |

| NAME | TYPE | | VALUE | | | ATTRIBUTES |
|---|---|---|---|---|---|---|
| DDLY. . . . . . . . . . | C | ADDR | ---- | | EXT | |
| DPFLAG. . . . . . . . . . | B | ADDR | 0001H.7 | R | PUB | SEG=DBRSEG |
| DPTADD. . . . . . . . . . | C | ADDR | ---- | | EXT | |
| DPTSUB. . . . . . . . . . | C | ADDR | ---- | | EXT | |
| DRSEG . . . . . . . . . . | D | SEG | 00CEH | | | REL=UNIT |
| DSPCOM. . . . . . . . . . | X | ADDR | 8000H | A | PUB | |
| DSPDAT. . . . . . . . . . | X | ADDR | 8001H | A | PUB | |
| ERNAN . . . . . . . . . . | | NUMB | 0003H | A | | |
| EROVF . . . . . . . . . . | | NUMB | 0002H | A | | |
| ERRMSG. . . . . . . . . . | C | ADDR | 0016H | R | | SEG=MYCSEG |
| ERUNF . . . . . . . . . . | | NUMB | 0001H | A | | |
| EXPVLA. . . . . . . . . . | D | ADDR | 000EH | R | PUB | SEG=DRSEG |
| F1COF . . . . . . . . . . | C | ADDR | 001EH | R | | SEG=MYCSEG |
| F1N . . . . . . . . . . | | NUMB | 0004H | A | | |
| F2COF . . . . . . . . . . | C | ADDR | 003EH | R | | SEG=MYCSEG |
| F2N . . . . . . . . . . | | NUMB | 0004H | A | | |
| F3COF . . . . . . . . . . | C | ADDR | 002EH | R | | SEG=MYCSEG |
| F3N . . . . . . . . . . | | NUMB | 0004H | A | | |
| FACBIT. . . . . . . . . . | D | ADDR | 000CH | R | PUB | SEG=DBRSEG |
| FACBTM. . . . . . . . . . | B | ADDR | 0003H.6 | R | PUB | SEG=DBRSEG |
| FACEXP. . . . . . . . . . | D | ADDR | 0007H | R | PUB | SEG=DRSEG |
| FACMAN. . . . . . . . . . | D | ADDR | 000DH | R | PUB | SEG=DRSEG |
| FACRNM. . . . . . . . . . | B | ADDR | 000CH.5 | R | PUB | SEG=DBRSEG |
| FACSGN. . . . . . . . . . | B | ADDR | 0000H.7 | R | PUB | SEG=DBRSEG |
| FACTMP. . . . . . . . . . | D | ADDR | 0005H | R | PUB | SEG=DRSEG |
| FBIAS . . . . . . . . . . | | NUMB | 007FH | A | | |
| FISHIN. . . . . . . . . . | C | ADDR | 01B0H | R | | SEG=MYCSEG |
| FIVE. . . . . . . . . . | C | ADDR | ---- | | EXT | |
| FLOAT . . . . . . . . . . | C | ADDR | ---- | | EXT | |
| FNCSEC. . . . . . . . . . | B | ADDR | 0001H.0 | R | PUB | SEG=DBRSEG |
| FNCSGN. . . . . . . . . . | B | ADDR | 0001H.1 | R | PUB | SEG=DBRSEG |
| FNCTM1. . . . . . . . . . | X | ADDR | 00C0H | R | PUB | SEG=XDRSEG |
| FNCTM2. . . . . . . . . . | X | ADDR | 00C4H | R | PUB | SEG=XDRSEG |
| FNCTM3. . . . . . . . . . | X | ADDR | 00C8H | R | PUB | SEG=XDRSEG |
| FP0 . . . . . . . . . . | C | ADDR | 0066H | R | | SEG=MYCSEG |
| FP1 . . . . . . . . . . | C | ADDR | 0072H | R | | SEG=MYCSEG |
| FP2 . . . . . . . . . . | C | ADDR | 0075H | R | | SEG=MYCSEG |
| FP5 . . . . . . . . . . | C | ADDR | 007AH | R | | SEG=MYCSEG |
| FP95. . . . . . . . . . | C | ADDR | 0075H | R | | SEG=MYCSEG |
| FPADD . . . . . . . . . . | C | ADDR | ---- | | EXT | |
| FPATN . . . . . . . . . . | C | ADDR | ---- | | EXT | |
| FPCMP . . . . . . . . . . | C | ADDR | ---- | | EXT | |
| FPCOS . . . . . . . . . . | C | ADDR | ---- | | EXT | |
| FPDIV . . . . . . . . . . | C | ADDR | ---- | | EXT | |
| FPEXP . . . . . . . . . . | C | ADDR | ---- | | EXT | |
| FPLN. . . . . . . . . . | C | ADDR | ---- | | EXT | |

While the present invention has been described in connection with a preferred embodiment, it is to be understood by one of ordinary skill in the art that modifications to this embodiment may be made, without departing from the spirit and scope of the present invention.

What is claimed is:

1. Apparatus for measuring total hemoglobin concentration and percent oxygen saturation in a sample of whole, undiluted blood, comprising:
   - an elongated cuvette for holding a whole undiluted blood sample;
   - means for selectively illuminating said blood sample with infrared light and red light, the infrared light and red light entering the cuvette at predetermined locations along an axis of the cuvette;
   - means associated with said cuvette for sensing infrared light intensity, IR, and red light intensity, R, at a predetermined measuring location along the axis of the cuvette remote from said predetermined locations at which the infrared light and red light enter the cuvette, and for generating signals indicative of IR and R;
   - processing means for receiving said signals and for calculating total hemoglobin (Hb), and percent oxygen saturation, SO2, based on the signals, (Hb) being calculated as a first calibrated function of IR, SO2 being calculated as a second calibrated function of (LogR/LogIR), the second calibrated function being related to the calculated (Hb).

2. The apparatus of claim 1, further comprising a housing for holding the illuminating means and detecting means, said housing having a bore for selectively retaining the cuvette.

3. The apparatus of claim 2, wherein the housing comprises a cylindrical block including an axial bore for selectively retaining the cuvette and radial bores for housing the means for selectively illuminating and said means for sensing.

4. The apparatus of claim 1, wherein the illuminating means comprise:
   - an infrared light source for emitting infrared light oriented substantially perpendicular to a longitudinal axis of the cuvette; and
   - a red light source for emitting red light oriented substantially perpendicular to the longitudinal axis of the cuvette.

5. The apparatus of claim 4, further comprising means for directing light from the cuvette to the means for sensing substantially as an exit light beam oriented perpendicular to the longitudinal axis of the cuvette.

6. The apparatus of claim 5, wherein the infrared and red light sources and light directing means are oriented whereby the infrared light and red light are laterally offset at selected angles in relation to the exit light beam.

7. The apparatus of claim 1, wherein the first calibrated function is a monotonic function.

8. The apparatus of claim 7, wherein the first calibrated function is a polynomial function approximated by the equation:

$$(Hb)=A_0=A_1IR+\ldots+A_nIR^n$$

wherein n is an integer greater than or equal to 2, and $A_0, A_1, \ldots, A_n$ are n+1 calibration constants.

9. The apparatus of claim 8, wherein n is 2.

10. The apparatus of claim 8, wherein n is 3.

11. A method for measuring total hemoglobin concentration and percent oxygen saturation in a sample of whole, undiluted blood, comprising:
    - selectively scattering infrared and red light through a whole, undiluted blood sample;
    - measuring infrared light intensity, IR, and red light intensity, R, at a predetermined location, such that total hemoglobin concentration, (Hb), is a monotonic function of IR:
    - approximating the monotonic function with a first calibrated equation;
    - calculating (Hb) from IR based on the first calibrated equation; and
    - determining a second calibrated equation for calculating percent oxygen saturation, SO2, as a function of (LogR/LogIR) based on the calculated (Hb).

12. The method of claim 11, wherein the first calibrated equation is a polynomial equation.

13. The method of claim 11, wherein the second calibrated equation is linear.

14. The method of claim 13, wherein the second calibrated equation is determined by:
    - determining a first intermediate equation representing the logarithm of R divided by the logarithm of IR for 0% oxygen saturated blood, $(LogR/LogIR)_{0\%}$, as a function of (Hb);
    - determining a second intermediate equation representing the logarithm of R divided by the logarithm of IR for 100% oxygen saturated blood, $(LogR/LogIR)_{100\%}$, as a function of (Hb);
    - calculating $(LogR/LogIR)_{0\%}$ corresponding to the calculated (Hb) based on the first intermediate equation;
    - calculating $(LogR/LogIR)_{100\%}$ corresponding to the calculated (Hb) based on the second intermediate equation;
    - calculating SO2 from the second calibrated equation, the second calibrated equation being:

$$SO2 = 100\frac{((LogR/LogIR) - (LogR/LogIR)_{0\%})}{((LogR/LogIR)_{100\%} - (LogR/LogIR)_{0\%})}$$

15. The method of claim 14, wherein the first intermediate equation is:

$$(LogR/LogIR)_{0\%}=C_0+C_1\,(Hb)+\ldots+C_n\,(Hb)^n$$

wherein n is an integer greater than or equal to 2 and $C_0, C_1, \ldots, C_n$ are n+1 calibration constants.

16. The method of claim 15, wherein n is 3.

17. The method of claim 14, wherein the second intermediate equation is:

$$(LogR/LogIR)_{100\%}=D_0+D_1\,(Hb)+\ldots+D_n(Hb)^n$$

wherein n is an integer greater than or equal to 2 and $D_0, D_1, \ldots, D_n$ are n+1 calibration constants.

18. The method of claim 17, wherein n is 3.

* * * * *